(12) United States Patent
Stiles et al.

(10) Patent No.: US 9,020,224 B2
(45) Date of Patent: Apr. 28, 2015

(54) VOLUME OF EFFICACY MODEL CAPTURE

(71) Applicant: Medtronic, Inc., Minneapolis, MN (US)

(72) Inventors: David Stiles, Danvers, MA (US); Jeffrey P. Bodner, Plymouth, MN (US); William F. Kaemmerer, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 189 days.

(21) Appl. No.: 13/714,550

(22) Filed: Dec. 14, 2012

(65) Prior Publication Data

US 2013/0287275 A1 Oct. 31, 2013

Related U.S. Application Data

(60) Provisional application No. 61/639,369, filed on Apr. 27, 2012.

(51) Int. Cl.
*G06K 9/00* (2006.01)
*G06T 7/00* (2006.01)
*G06F 19/00* (2011.01)
*A61B 6/00* (2006.01)

(52) U.S. Cl.
CPC .......... *G06T 7/0012* (2013.01); *G06F 19/3437* (2013.01); *G06F 19/3468* (2013.01)

(58) Field of Classification Search
CPC ................................... G06K 9/00; G06T 7/00
USPC ......... 382/128, 129, 130, 131, 132, 133, 134; 378/65, 21–27, 101, 901; 600/1, 9, 21, 600/23, 26, 39, 411, 425, 427, 439, 431
See application file for complete search history.

(56) References Cited

U.S. PATENT DOCUMENTS

| 5,740,808 | A | 4/1998 | Panescu et al. |
| 5,964,705 | A | 10/1999 | Truwit et al. |
| 5,983,126 | A | 11/1999 | Wittkampf |
| 6,026,316 | A | 2/2000 | Kucharczyk et al. |
| 6,381,485 | B1 | 4/2002 | Hunter et al. |
| 6,464,662 | B1 | 10/2002 | Raghavan et al. |
| 6,482,182 | B1 | 11/2002 | Carroll et al. |
| 6,493,573 | B1 | 12/2002 | Martinelli et al. |
| 6,516,212 | B1 * | 2/2003 | Bladen et al. .................. 600/424 |

(Continued)

FOREIGN PATENT DOCUMENTS

| EP | 1768062 A1 | 3/2007 |
| EP | 07106176 | 4/2007 |

(Continued)

OTHER PUBLICATIONS

BrainLab. 2006 BrainLab AG. Printed in Germany. NS-FL-E-iPlanFLOW Rev. 2.0506 Q:2.000. (2 pages).

(Continued)

*Primary Examiner* — Abolfazl Tabatabai
(74) *Attorney, Agent, or Firm* — Harness, Dickey & Pierce, P.L.C.

(57) ABSTRACT

A system and method for determining, planning, and/or administering a therapy of a selected material from a catheter to a selected specific region of an anatomy is disclosed. The catheter can be used to deliver a drug to the patient to achieve a volume of efficacy (VOE) within a selected target, region, or volume. The drug delivered can be used for treating at least a symptom in the patient.

37 Claims, 9 Drawing Sheets

(56) References Cited

U.S. PATENT DOCUMENTS

| | | |
|---|---|---|
| 6,549,803 B1 * | 4/2003 | Raghavan et al. ............ 600/431 |
| 7,371,225 B2 | 5/2008 | Oldfield et al. |
| 7,570,791 B2 | 8/2009 | Frank et al. |
| 7,715,902 B2 | 5/2010 | Hartlep et al. |
| 7,751,865 B2 | 7/2010 | Jascob et al. |
| 7,835,778 B2 | 11/2010 | Foley et al. |
| 8,112,292 B2 | 2/2012 | Simon |
| 8,295,914 B2 * | 10/2012 | Kalafut et al. ................ 600/431 |
| 2003/0114752 A1 | 6/2003 | Henderson et al. |
| 2005/0049486 A1 | 3/2005 | Urquhart et al. |
| 2005/0085714 A1 | 4/2005 | Foley et al. |
| 2005/0085720 A1 | 4/2005 | Jascob et al. |
| 2008/0081982 A1 | 4/2008 | Simon et al. |
| 2009/0270712 A1 | 10/2009 | Raghavan et al. |
| 2010/0240986 A1 | 9/2010 | Stiles |
| 2012/0209110 A1 | 8/2012 | Bankiewicz et al. |
| 2013/0287272 A1 | 10/2013 | Lu et al. |
| 2014/0171781 A1 | 6/2014 | Stiles |
| 2014/0171900 A1 | 6/2014 | Stiles |

FOREIGN PATENT DOCUMENTS

| | | |
|---|---|---|
| EP | 1788499 A1 | 5/2007 |
| EP | 1980201 A2 | 10/2008 |
| WO | WO-2011008982 A1 | 1/2011 |
| WO | WO-2012116747 A1 | 9/2012 |

OTHER PUBLICATIONS

Cabezas, et al. "Areview of atlas-based segmentation for magnetic resonance brain images." Computer Methods and Programs in Bioomedicine. (2011) pp. e158-e177.

Documentation/4.1—SlicerWiki, http://wiki.slicer.org, (2012) p. 1-6.

Linninger, et al., "Annals of Biomedical Engineering." 2007.

Linninger, et al., "Mimic Image Reconstruction for Computer-Assisted Brain Analysis," 2005.

Linninger, et al., "Neurosurg," Focus, 2006, vol. 20.

Morrison PF, et al., "High-flow microinfusion: tissue penetration and phar-acodynamics." Am J Physiol, 1994, vol. 266, R292-R305.

Morrison PF, et al., "High-flow microinfusion: tissue penetration and phar-macodynamics."Am J Physiol, 1994, vol. 266, R292-R305.

Sampson, JH, et al. "Colocalization of gadolinium-diethylene triamine pentaacetic acid with high-molecular-weight molecules after intracerebral convection-enhanced delivery in humans." Neurosurgery, Sep. 2011; 69(3):668-76.

Synchromed II—Infusion system patient manual. (2003) pp. 1-72.

Xiaomin ,Su, et al. "Real-time MR Imaging with Gadoteridol Predicts Distribution of Transgenes After Convection-enhanced Delivery of AAV2 Vectors." The American Society of Gene & Cell Therapy.www.moleculartherapy.org., vol. 18 No. 8, 1490-1495, Aug. 2010.

International Search Report and Written Opinion mailed Jul. 16, 2014 for PCT/US2013/073655 claiming benefit of U.S. Appl. No. 13/714,555, filed Dec. 14, 2012.

International Search Report and Written Opinion for PCT/US2013/073676 mailed Jul. 16, 2014 (claiming benefit of U.S. Appl. No. 13/714,563, filed Dec. 14, 2012).

* cited by examiner

VOLUME OF EFFICACY MODEL CAPTURE

CROSS-REFERENCE TO RELATED APPLICATIONS

This application claims the benefit of U.S. Provisional Application No. 61/639,369, filed on Apr. 27, 2012. The entire disclosure of the above application is incorporated herein by reference.

FIELD

The subject disclosure relates to delivering a therapy of a selected material; and particularly to determining and modeling a volume of efficacy based on selected factors within a selected anatomy of a patient and determining the factors to achieve a selected volume of efficacy in a selected location.

BACKGROUND

In various therapy applications, a selected therapy can be applied to a patient to achieve a selected result or therapeutic effect. The therapeutic effect can include orally administering a pharmaceutical, such as a pain inhibitor, to reduce pain felt by a patient. Other pharmacological treatments can include delivery intravenously of selected drugs, such as chemotherapy drugs and other selected pharmacological agents. Generally, a pharmaceutical can be delivered orally or intravenously to the anatomy of the patient but are not delivered directly to the area of interest within the patient.

Various procedures, however, may be selected for efficiency or specific regions of activation. For example, deep brain stimulation (DBS) probes can be introduced into a patient to stimulate selected and specific regions of a brain. In patients diagnosed with Parkinson's, DBS probes can be implanted into the brain to stimulate a selected region of the brain to reduce Parkinson's symptoms. A region of activation can be determined based on electrical properties introduced through the DBS probe. The electrical properties, however, are dependent upon the input of electrical parameters, such as pulse width and voltage, into the tissue of the brain. Such therapies do not deliver a material from the probe, but rather only stimulate the neurological tissue with an electrical signal.

In some instances, intrathecal delivery catheters are known to deliver a drug, such as the muscle relaxant and antispastic sold as LIORESAL®, with a drug pump. Drug pumps include the SYNCHROMED® II pump sold by Medtronic, Inc. The drug can be delivered by a catheter to a patient.

SUMMARY

A pharmacological therapy can be delivered from a catheter to a selected specific region of an anatomy. For example, a catheter can be introduced into a patient's anatomy, either for an acute or immediate therapy or to dwell in the patient for a chronic therapy. The catheter can be used to deliver a drug to the patient to achieve a volume of efficacy (VOE) within a specific selected target, region, or volume. The selected target, region or volume can be based upon a known area that is afflicted with a disease which should be treated with the selected therapy. Various drugs can be delivered to a patient through a catheter in an attempt to achieve the VOE at the selected area or volume.

The VOE of a pharmaceutical treatment is the volume in which the drug is deemed or shown to have a local parenchymal concentration that is effective for treatment of a symptom or disease. The VOE for a pharmaceutical treatment can be based on various parameters, such as flow rate, concentration, and the like of a pharmaceutical being delivered through a catheter. Generally, the drug being delivered will include a mass transport variable or aspect based upon delivery of the pharmaceutical, in addition to a pharmacodynamic (PD) and a pharmacokinetic (PK) aspect or property. These aspects, including the PK, PD, and mass transport can be used to model or predict the VOE within a patient. The predicted VOE can be used to analyze a location or select a location of the catheter to achieve the VOE at the selected anatomical target for therapy.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings. Corresponding reference numerals indicate corresponding parts throughout the several views of the drawings.

DETAILED DESCRIPTION

Figure 1:
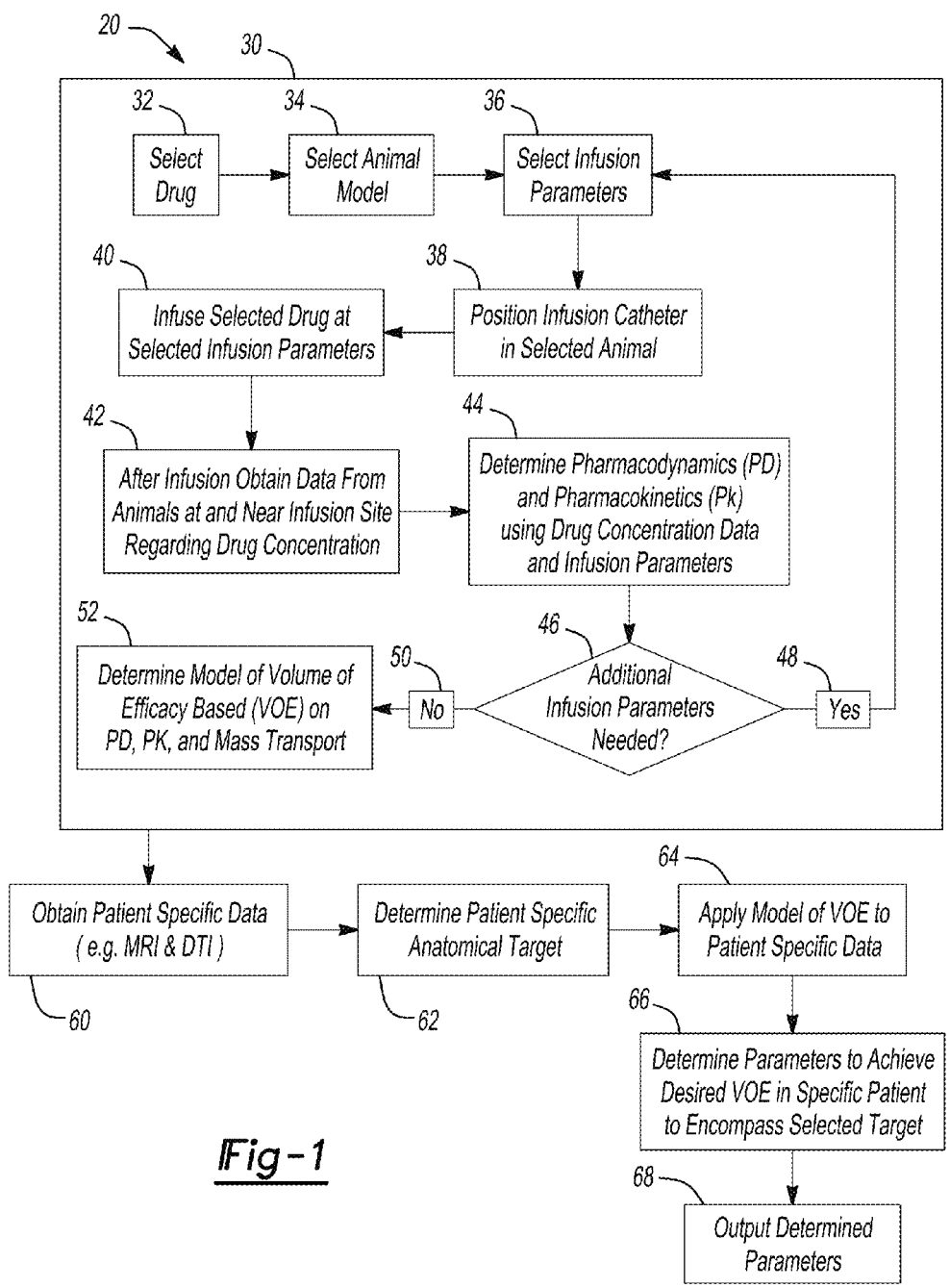
FIG. 1 is a flowchart relating to a process for determining and applying a VOE prediction.

With reference to FIG. 1, a flowchart 20 includes a process for determining aspects of a particular drug to determine a volume of efficacy (VOE) and the application of the VOE to a selected patient. Generally, in a first or sub-protocol 30, a VOE model of a particular drug can be determined. A model for a particular drug can be limited to the various selected parameters of the drug. For example, a chemotherapy chemical may include different characteristics, such as a pharmacodynamic (PD) and/or pharmacokinetic (PK) aspect that differ from a siRNA molecule. Accordingly, the VOE model determined in sub-routine 30 can be repeated or determined for any plurality of drugs or pharmaceutical agents that may be used to treat selected patients. It is also understood herein that a drug may include any material delivered through a catheter or other instrument as discussed herein, and can include biological molecules or analogues (e.g., siRNA) or other chemical agents (e.g. antibiotics and diagnostic molecules). Diagnostic molecules can be those, such as traceable agents, that assist in determining at least one of PD and PK in a patient.

The VOE is generally determined to be the physical volume of a concentration of a material (e.g., a drug, therapy material, or the like) that is efficacious for treating a disease.

For example, an effective concentration for treating a disease or ailment can be determined. The volume of efficacy is therefore the volume in a subject that includes the efficacious concentration of the material. A volume of efficacy can be determined based upon various factors, including the PK and PD, flow rate and flow parameters, and other factors as discussed further herein. Accordingly, the VOE can be determined in a subject, such as a human patient, based upon these various factors in the tissue into which it is injected. Further, the VOE can be shown as a graphic icon on a display. In addition, the VOE icon can be shown superimposed on image data of a patient or subject to illustrate the physical volume relative to the image data in the patient as the VOE. Accordingly, the VOE is generally determined to be the volume that relates to an efficacious concentration of a material. It is further understood that a volume of distribution (VOD) of a selected material may be greater than the VOE. In other words, the concentration of the material is less than an efficacious concentration but still may be present in the subject. Accordingly, the VOD can also be determined and illustrated as an icon either alone or superimposed on image data of the patient.

Accordingly, a first step of the sub-routine 30 can be selecting a drug in block 32. An animal model can then be selected in block 34 to determine a specific PD and PK in selected anatomical tissues for the disease being considered. Animal models can include rat animal models, simian animal models, and other selected animal models. For example, rhesus monkeys (*Macaca mulatta*) can be used to determine PK and PD that can be translated to human patients for the drugs selected in block 32.

After the animal model has been selected in block 34, such as a Rhesus Monkey animal model, an infusion parameter or a plurality of infusion parameters can be selected in block 36. Infusion parameters can include high flow rate, low flow rate, time at high flow rate, time at low flow rate, and drug concentration. Other parameters can also be considered for determination of the VOE including clearance rate of the molecule, in situ rate of metabolic degradation of the molecule, rate of internalization of the molecule within various cellular structures in the vicinity of the anatomical target and time-to-concentration-steady-state. In addition, PD rates of target (receptor, enzyme, etc.) engagement, time-dependent parenchymal concentration versus drug effect correlations, time to baseline (where baseline is the state of the anatomy or tissue prior to the presence of the drug). The parameters can be selected and set for the subroutine 30 to determine the VOE and related PK and PD, as discussed further herein. It is understood, however, that these can be altered and optimized during various iterations to verify or further determine the PK and PD of selected drugs.

With continued reference to FIG. 1 and the subroutine 30, once the infusion parameters have been selected in block 36, an infusion catheter can be positioned in a selected animal of the animal model in block 38. Positioning of an infusion catheter can include implanting for chronic drug delivery (e.g., implanted catheter and pump system) or positioning for an acute therapy by a catheter within the selected animal. Additionally, positioning the catheter can include selecting a catheter to have various properties. For example, a catheter can include one or more infusion ports or include a porous perfusion catheter tip. The type of catheter can affect the delivery of the material from the catheter into the patient which can alter the VOE. A catheter having a single port generally will deliver a selected material in a single location and/or direction and rely on the properties of the material in the anatomy into which it is infused to move the material. A catheter including multiple ports or exits and/or a perfusion tip will deliver a material to a wider range of positions and volume without requiring action or interaction of the perfused material in the anatomy of the patient.

After the infusion catheter is positioned in block 38, the selected material or drug can be infused in block 40. The infusion of the drug can be through the catheter at the selected positions in block 38 and according to the parameters selected in block 36. Accordingly, the selected drug delivered through the catheter is delivered with the selected infusion parameters including the flow rate, concentration and other infusion parameters. The chronic infusion of the selected drug can occur for any appropriate period of time, such as a few months to a few years or continuously for the life of the patient. Generally, the infusion will not change from the selected infusion parameters for the entire time period, although the dosing regimen may be modified to account for morphological or physiological changes due to the patient or the disease. It is understood, however, that acute infusion can occur by delivering a selected volume of the selected drug at a selected small time period according to the selected infusion parameters. Accordingly, the infusion may have a time period of 30 minutes, 1 hour, 2 hours, 12 hours, 24 hours and other selected time periods than an infusion can happen entirely at the selected infusion parameters.

Subsequent to the infusion of the selected drug, measurements can be made in the animal model including a volume having a selected concentration of the drug. The selected concentration can relate to an efficacious concentration where the efficacious concentration relates to a concentration of a drug that achieves selected results within a patient. Accordingly, after the drug is infused in block 40, data can be obtained from the animal near the infusion site or relative to the infusion site to determine a volume of efficacy based upon the infusion parameters in block 42. For example, an entire organ can be studied to determine a concentration at all locations of the organ. The organ can be studied at a selected interval from the time of the beginning of the infusion.

Figure 2:
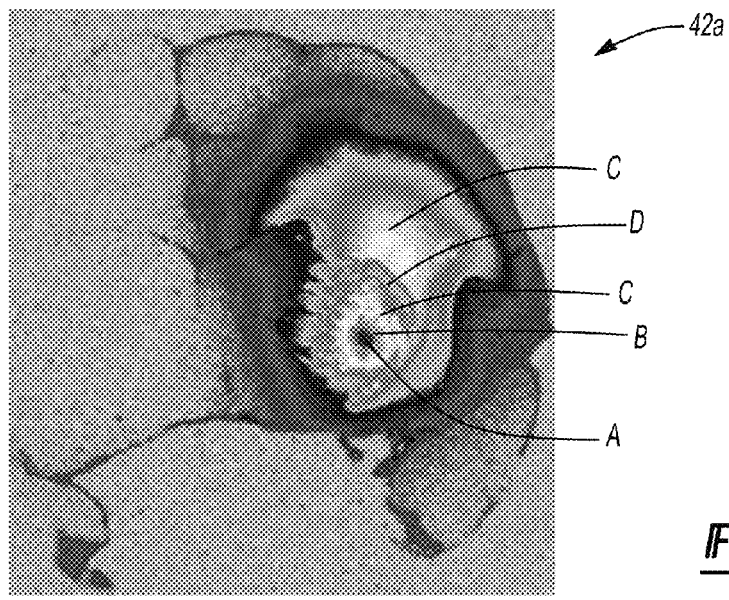
FIG. 2 is a schematic illustration local parenchymal concentration used in the determination of a volume of efficacy.

Determining the volume of efficacy can be performed by various techniques. With reference to FIG. 2, for example, an animal can be sacrificed and slices of tissue can be taken and the concentration of drug can be measured or determined in an area extending from the catheter placement site. As illustrated in FIG. 2, a measurement of a slice 42a is illustrated. The measurement can include several areas of differing concentrations or illustrate concentration gradients. For example, A, B, C, and D can each illustrate areas that differ in concentration by 10% or by some selected absolute concentration amount, for example 0.1 picoliter/gram of tissue, where, in the exemplary slice 42a, A is the highest concentration and D is the lowest. The measurement can include radio labeling a molecule (e.g. with Carbon 14) and then measuring the concentration of the radioactivity in the different areas. The VOE can be determined to be the volume in which the drug is at some selected or determined concentration. Generally, the VOE is that volume in which the drug is at least at a concentration to effectively treat a selected local pathophysiology or symptom.

The concentration of the drug can be determined in the tissue slices and in three-dimensional space relative to the placement of the catheter to determine an efficacious concentration of the drug in a three-dimensional location relative to the catheter placement. As a part of the determination of volume of efficacy, the concentration of the drug in the area or volume relative to the catheter can be discretely measured at discrete three-dimensional points relative to the position of the catheter. The discrete three dimensional location of a measured concentration relative to the catheter can be stored for model creation and use, as discussed further herein. Accordingly, a volume of efficacy can be determined in block 42 relative to the position of the catheter in the animal model. Additionally, or in combination with measuring drug concentrations in tissue slices, other image data or testing analyses can be performed on the animal model to determine a volume of efficacy and drug characteristics.

A volume of efficacy determined in block 42 can be used to determine pharmacodynamics (PD) and pharmacokinetics (PK) based upon the VOE and infusion parameters used in block 44. The PD and PK can be determined based upon analyses of concentration of the drug relative to the position of the catheter within the animal model. In other words, the VOE can illustrate the effect of the drug, the absorption, and other characteristics of the drug in the tissue. Additionally, the PK and PD can be determined for various types of tissue based upon the concentration and speed of the drug movement into the different tissues surrounding the catheter site. The PD and PK of a drug may differ based upon tissue types and anatomy into which the drug is placed. Thus, the determination of the PD and PK can be used in a predictive model, as discussed herein, to predict a VOE in identified tissues. Additionally, the catheter can be positioned in specific selected types of tissue, such as white matter or gray matter, and the PK and PD in the specific tissues can be determined.

The determination of the VOE, the PK, and the PD can be enhanced or refined based upon whether additional infusion parameters are needed in block 46. If additional parameters are needed, such as to enhance or further refine or verify the PK, PD and VOE determination, a YES path 48 can be followed to select infusion parameters in block 36 that can be different from initial or previous infusion parameters. Once new parameters are selected, the infusion and measurement steps in blocks 38-44 can be repeated. It is further understood that a new position of the catheter can also be determined or selected in block 38. A new position of the catheter can include moving the catheter between different types of tissue, such as white matter to grey matter.

Figure 7:
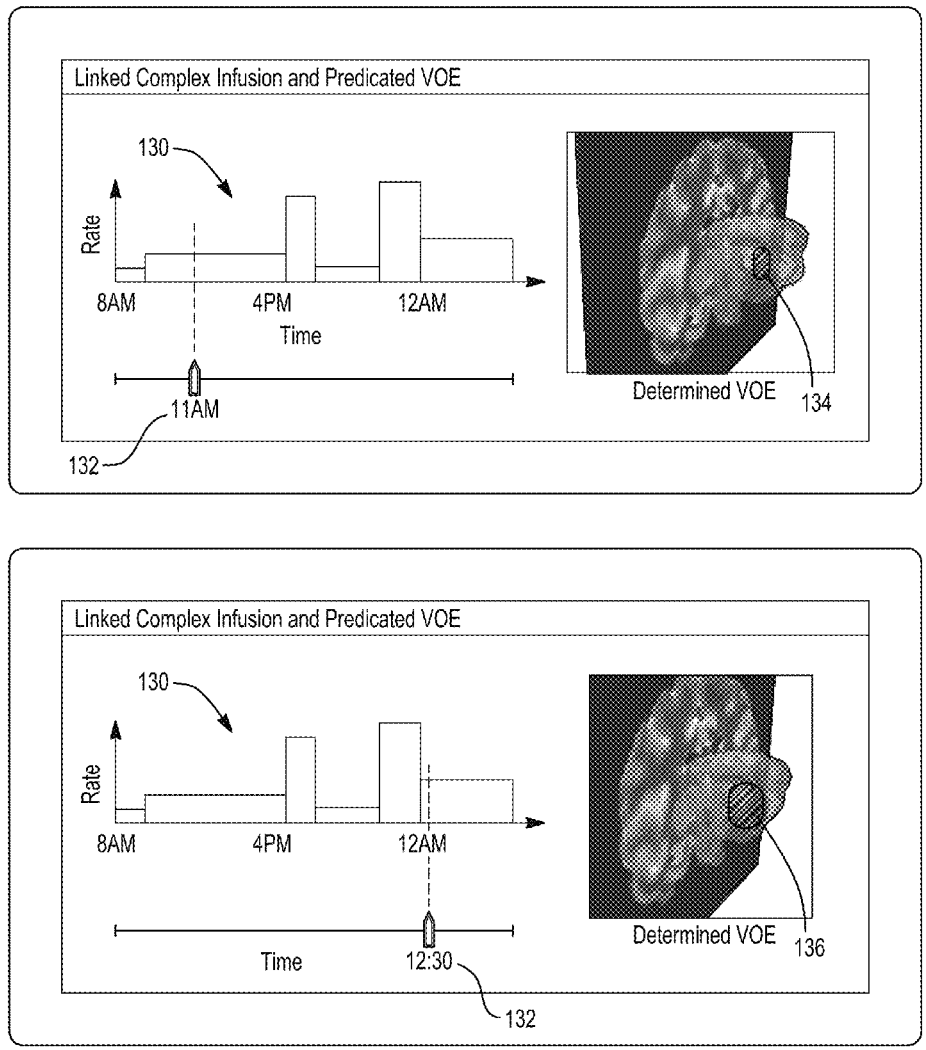
FIG. 7 is a screen shot of an output/input screen.

Complex parameters can also be determined or evaluated in block 51. Complex parameters can include those parameters that change over time, as illustrated in FIG. 7. Parameters that can change include infusion rate, concentration, and other parameters that can change over time. The parameters that can change over time can change the VOE, as well, over time. This can be useful, for example, for when placing a catheter in a specific portion of the brain is not be possible or difficult. When a catheter or instrument can be placed in the exact desired location, it can be selected to increase the flow rate to infuse the selected material to encompass the specific anatomic target. After a selected time period, the infusion rate can be reduced so that the VOE decreases and no longer encompasses the selected anatomical target to decrease administration of the selected material to unselected tissues. Thus, infusion parameters can be both selected for determining a VOE, but can also be selected to vary over time to achieve a varying VOE relative to the specific target made in block 62. If it is determined that no additional infusion parameters are needed to determine the PK, PD, or the VOE then a NO path 50 can be followed to determine a model VOE in an anatomy based upon the PD and PK along with mass transport determinations in block 52. The mass transport determination or selected calculation can include fluid dynamic calculations or measurements including pump force or volume delivered. The determined PK and PD, determined in part due to the evaluation of the VOE measured in block 42, can be incorporated into a predictive model for determining VOE in an anatomy different from those used to determine the model. As discussed further herein, the determined model of the VOE can be used to predict a VOE in a specific patient based upon the determined PD and PK from the animal model from the analyses performed from the subroutine 30. Accordingly, the subroutine 30 can be used to determine a model, such as a mathematical or computer algorithm model, to predict a VOE within a selected patient or anatomical region.

For example, the subroutine 30 can be used to determine a model of a VOE for use in a specific patient. Accordingly, specific patient information can be obtained in block 60. Specific patient information can include image data information, such as magnetic resonance image (MRI) or computer tomography (CT) image data information. Additional specific patient information can include anatomical or physiological information such as diffusion tensor imaging (DTI) data. DTI data can be used to analyze the type of tissue and the position of the tissue within the anatomy of the specific patient. As a PD and PK of a drug can differ or be used to determine a movement, growth, and/or shape of a VOE within different types of anatomical tissues, the DTI data can be used to enhance or apply the model in the specific patient.

Based upon a disease to be treated and the patient-specific information obtained in block 60, a specific anatomical target can be determined in block 62. For example, a putamen can be selected as a specific anatomical target within a specific patient. The putamen can be selected to have a drug delivered thereto or at least to have a VOE substantially surround and/or within the putamen. It will be understood that other anatomical targets can be selected, such as an entire volume of a patient's brain, or caudate, or other target selected. Target selections can be based upon an analysis and determination of a disease of the specific patient to be treated or a drug or other material to be delivered to the patient. Nevertheless a specific target can be determined in the patient to be covered by the VOE.

Thus, the model based on output of the subroutine 30 can be applied to the patient-specific data to have the VOE include the selected target in block 64. By applying the model to the specific patient, the determination of a VOE in a specific patient can be made. The VOE model can include the PK and PD that are specific to a drug and can be used to determine the location of the VOE in a specific patient. The application of the model to the specific patient can be used to determine a location of a catheter for infusing and the infusion parameters to include the selected target within the VOE.

After applying the model to the specific patient, a determination of procedure parameters to achieve a selected VOE in the specific patient at the selected target can be made in block 66. The determined procedure parameters can include the procedure infusion parameters and a position of the catheter that are selected to achieve the selected VOE. The procedure infusion parameters can include, as discussed above, high and low flow rates, times at the high and low flow rates, and concentration of the material to be infused. The parameters in combination with the model using the PD and PK can be used to model the VOE relative to the location of the catheter. The selected VOE is selected, at least generally, to be formed relative to the selected target. For example, the selected VOE can substantially encompass or include the entire volume of the selected target. Substantially encompassing can include ensuring that 100% of the selected target is within the modeled VOE. In addition, or alternatively, substantially encompassing can include ensuring that at least a minimum percentage and/or selected portion of the target are within the modeled VOE.

The determined procedure parameters can then be output in block 68. The determined procedure parameters output in block 68 can be output for performing a procedure by a surgeon or for programming an implanted pump for chronic delivery of a material. The output determined procedure parameters can include both the procedure infusion parameters and the position of the catheter.

As discussed above, the method 20 illustrated in FIG. 1 may be used to determine or model a predicted VOE in a specific area (e.g. organ or portion of an organ) of a specific patient using information acquired from various models and/or general animal models. The model generated from the subroutine 30 allows the modeled or predicted VOE to be determined for a specific patient or anatomical specimen. Data from animal models can be acquired by using a radioactive isotope of a specific molecule, such as a siRNA, that is infused from a catheter into the specific animal model. The infusion can happen within a specific animal model, as disclosed in block 40 based upon selected infusion parameters selected from block 36.

At selected time intervals after the beginning of the infusion, various or numbers of the selected animal model members can be sacrificed for study. An organ into which the infusion is occurring, for example, the brain of the animal, can then be studied. In various embodiments, the brain can be sliced and the slices can then be analyzed, as discussed in block 42, to determine a concentration gradient relative to the infusion catheter site. The concentration gradient can be determined in three-dimensions relative to the catheter infusion site. In various embodiments, a concentration at specific three-dimensional spatial locations relative to the position of the catheter where infusion occurred can be determined. Accordingly, the concentration at the various specific and three dimensional locations can be determined and used to identify a model of movement of the drug into the tissue. The gradient can be used to identify a boundary of a selected or efficacious concentration of the drug.

In addition, the types of tissue can be analyzed to determine and model differences of movement of the drug in different types of tissue. For example, a brain may be non-uniform including both white and grey matter. Thus, movement of a liquid in the different tissues may differ. Accordingly, the model can then account for specific tissue which are also analyzed and identified in the patient-specific information obtained in block 60 to predict the VOE in the specific patient.

Once the analysis is acquired, the PK and PD can be determined in block 44 to determine a predictive model for the VOE in block 52. The PK and PD can be determined based on the analysis of the data from the animal model studies. A predictive model determined in block 52 uses the PK and PD alone or with other parameters to predict a movement of the drug in a specific patient, as discussed below. Generally, the PK and PD are determined values for variables in a calculation, and the calculation, as a part of the determined predictive model, can be used to predict a VOE in a specific patient.

Figure 3:
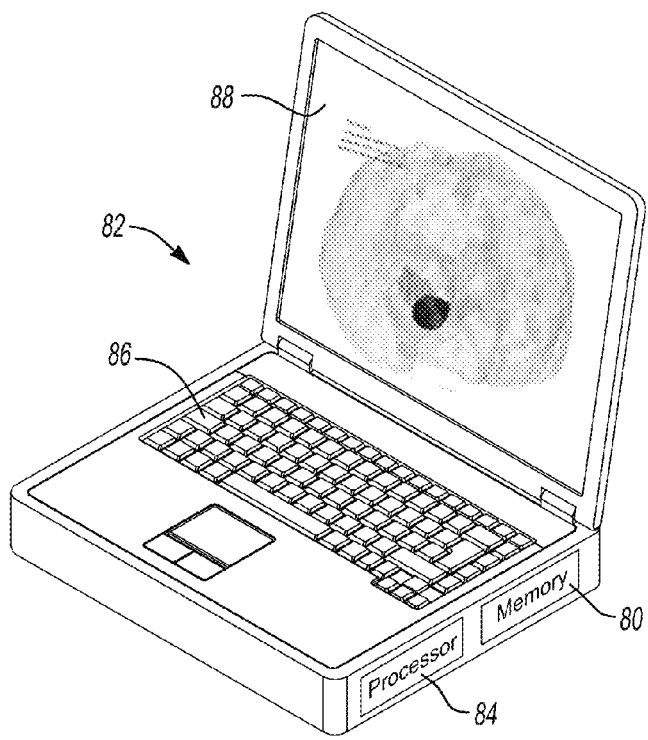
FIG. 3 is a schematic of a system to execute an algorithm and display a result.

The model can be stored as constants for fluid flow and mass transit equations as for an algorithm in a memory system 80, as illustrated in FIG. 3. The memory 80 can be a part of a computer system 82 or accessible therewith to allow a processor system 84 to execute the algorithm stored on the memory 80. In addition, the processor 84 can access patient-specific data obtained in block 60 to determine a predicted patient-specific VOE in block 66. The patent-specific data can be stored in the memory 80 or separately and accessed by the processor 84. Additionally, a user input, such as a keyboard 86, can be used to input patient-specific information and to identify a patient-specific selected target in a patient specific data from block 60.

As discussed herein, the determined predictive model of VOE can be used to determine a VOE in a specific patient based on the calculated vales of PD and PK (from the subroutine 30) and the patient specific data from block 60. A display 88 can be used to display an icon of the modeled predicted patient-specific VOE either separate from or superimposed on image data. The modeled predicted patient-specific VOE can be based upon the model determined at block 52 and the patient-specific target determined in block 62 that is determined from the patient specific data from block 60. Thus, the determined PD and PK that are incorporated into the determined model in block 52 are used to model and predict the VOE in the specific patient. The modeled predicted patient-specific VOE can also be based on a position of an infusion catheter and, therefore, the modeled predicted patient-specific VOE can also analyze and/or select a catheter position to encompass the selected target from block 62.

Figure 4:
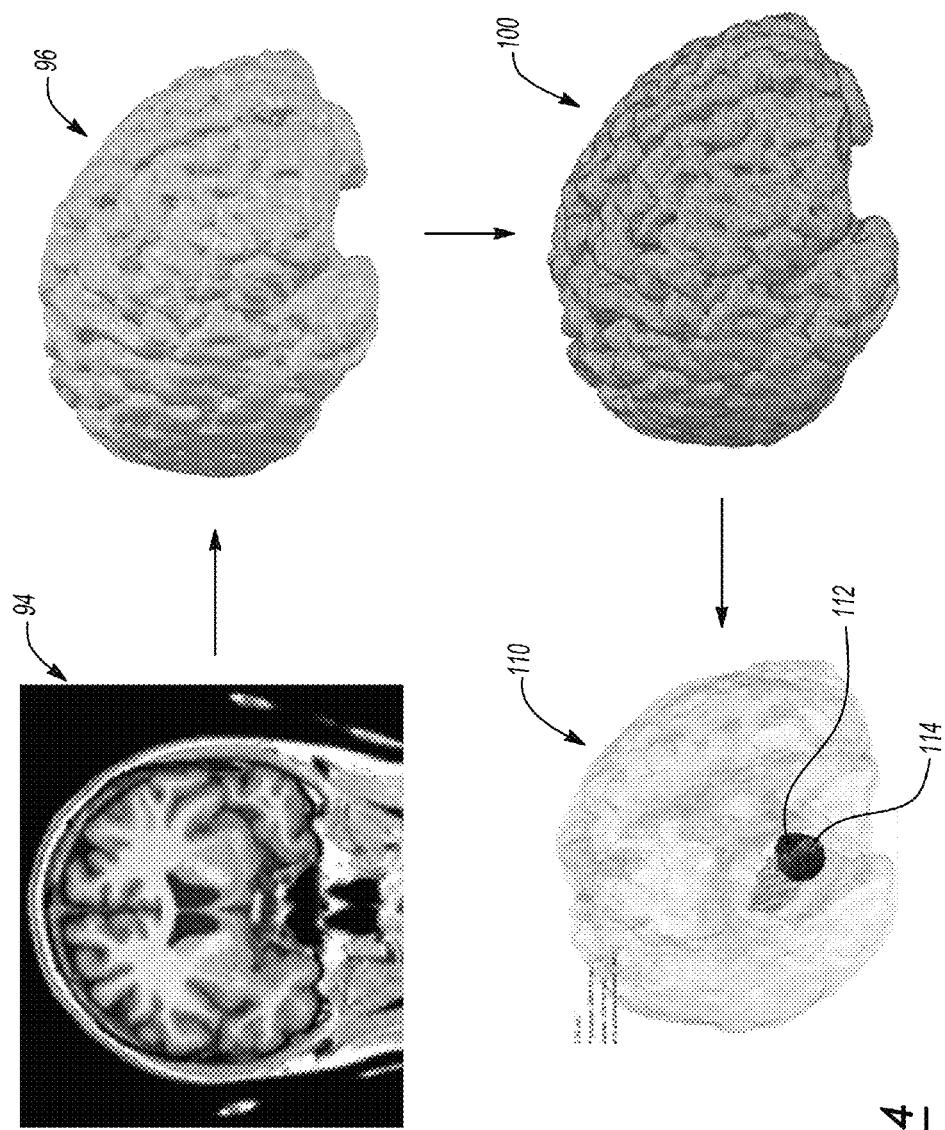
FIG. 4 is a flowchart illustrating application of a predictive algorithm and output therefrom.

With continued reference to FIGS. 1 and 3, and additional reference to FIG. 4, the obtained patient-specific information from block 60 can include MRI image data 94. Patient-specific MRI image data can be used to assist a user in selecting or determining a patient-specific target from block 62, and also in identifying various tissues for application of the model from block 52. In addition, patient-specific data can include a disease of a patient, a drug to be infused into a patient, and other selected patient-specific information. The patient-specific information, including the image data, can then be processed or rendered by the processor 84 or other selected computer processors. The image processing can be used to generate a three-dimensional model of the image data, as illustrated at 96. It is understood that the patient-specific image data 94 and the 3D model 96 can be illustrated on the display 88.

A filled mesh 100 of the 3D model 96 can be used to analyze the patient-specific information (e.g. MRI image data 94) obtained in block 60 and the anatomical target has been determined in block 62 using the model from block 52 to determine the modeled predicted patient-specific VOE in block 64. The filled mesh 100 can include identification of tissues and/or anatomical structures, tissue properties (e.g. densities), and other properties of tissue in the portions of the 3D model 96 based on the specific patient image data 94. In other words, the filled mesh 100 allows for analysis of discrete volume portions of the patient based on the patient specific data, including image data. For example, the identification of tissue properties within the patient based on the MRI and DTI data. The VOE model can include the values of the PD and PK along with other mass transport information. In one convection-diffusion equation, Equation 1, $$\varphi \frac{\partial c}{\partial t} + \nabla \cdot (vc) = \varphi D \nabla^2 c + S \qquad \text{Eq. 1}$$

is used to predict and model a VOE in the specific patient. It is understood that the mass transport Eq. 1 can be derived or augment for selected procedures or materials including fluid flow in different materials. The terms of Eq. 1 are discussed herein and allow for determination of the VOE in a specific patient due to the identification of the tissue properties, etc. of the patient based on the patient specific data. As discussed herein, the use of the PD and PK values along with other calculations can be used to illustrate the predicted VOE in a specific patient based on the patient specific information (e.g. tissue properties and type) from the patient specific data.

The model from block 52 is used to determine the parameters, including those discussed above, to achieve the modeled predicted patient-specific VOE to encompass the selected target. The parameters can include those discussed above, including high and low flow rates, time at high and low flow rates, and concentration of the drug. In addition, location and/or number of outlet holes of the catheter can be evaluated and determined. For example, a single outlet, multiple outlet, or perfusion catheter can be analyzed. In addition more than one catheter emanating from the same pump could be used to distribute a dose of a drug. Additional parameters can include the average or maximum target knockdown of the infused drug.

Instructions, such as computer instructions, for predictive model for the VOE determined in block 52 can be executed to determine the modeled predicted patient-specific VOE which then can be output in block 68 and illustrated on display 88 as a solution display 110. The solution display 110 can include an illustration of the modeled predicted patient-specific VOE as a modeled predicted patient-specific VOE 112 and a catheter icon 114 to illustrate a selected location of a catheter for infusion. Accordingly, the output solution or illustration 110 can output the modeled predicted patient-specific VOE 112 for analysis by a user, such as a surgeon, to determine whether a different catheter location or different parameters should be selected.

Further, the output display 110 can be used by a user to ensure an appropriate coverage of the selected target from block 62. As discussed above, the VOE relates to a volume where the drug is at a concentration that is determined to effect or effectively treat a symptom or disease. Thus, the illustrated VOE 112 can include a volume that includes several or differing drug concentrations, but the boundary of the VOE 112 can be at a selected low threshold concentration. It will also be understood that the output parameters can include the type of catheter, the flow rates, concentration of the drug, times of the various flow rates, and other selected parameters. Thus, the output solution can include the output parameters from block 68 to be used as a part of a procedure to treat a patient.

Figure 5:
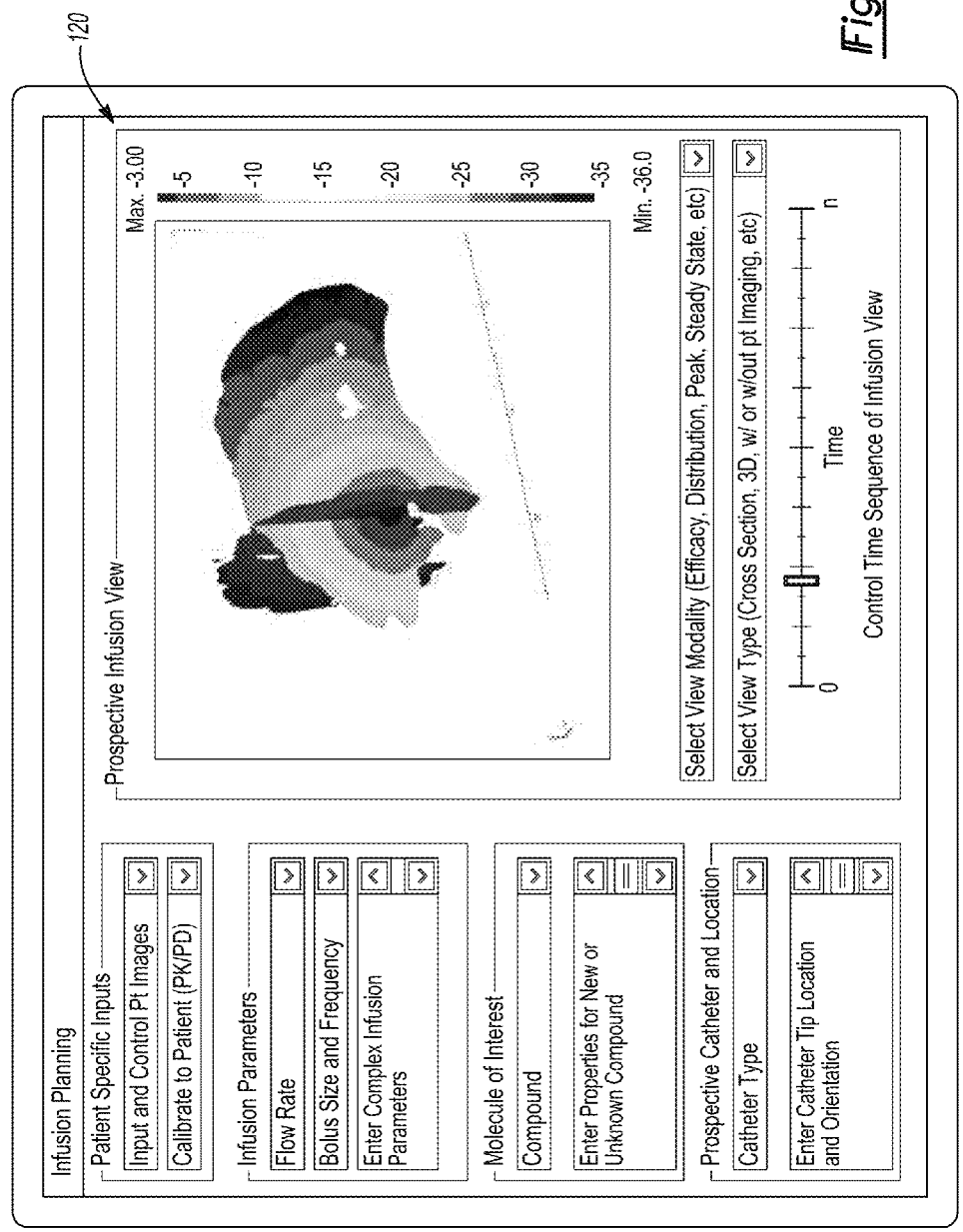
FIG. 5 is a screen shot of an output/input screen.

The output of parameters from block 68, as discussed above, can be illustrated on the display device 88, such as the output solution 110. The output parameters can include a plurality of possible output solutions or information. For example, as illustrated in FIG. 5 an illustrative output/input screen 120 of outputs and possible inputs to vary the outputs can be displayed. The combination output/input screen 120 can include controls to input patient image data, infusion parameters, molecules of interest (e.g. the drug), possible catheter location, and a portion of the output/input screen 120 can be used to view the predicted or prospective VOE.

Figure 6:
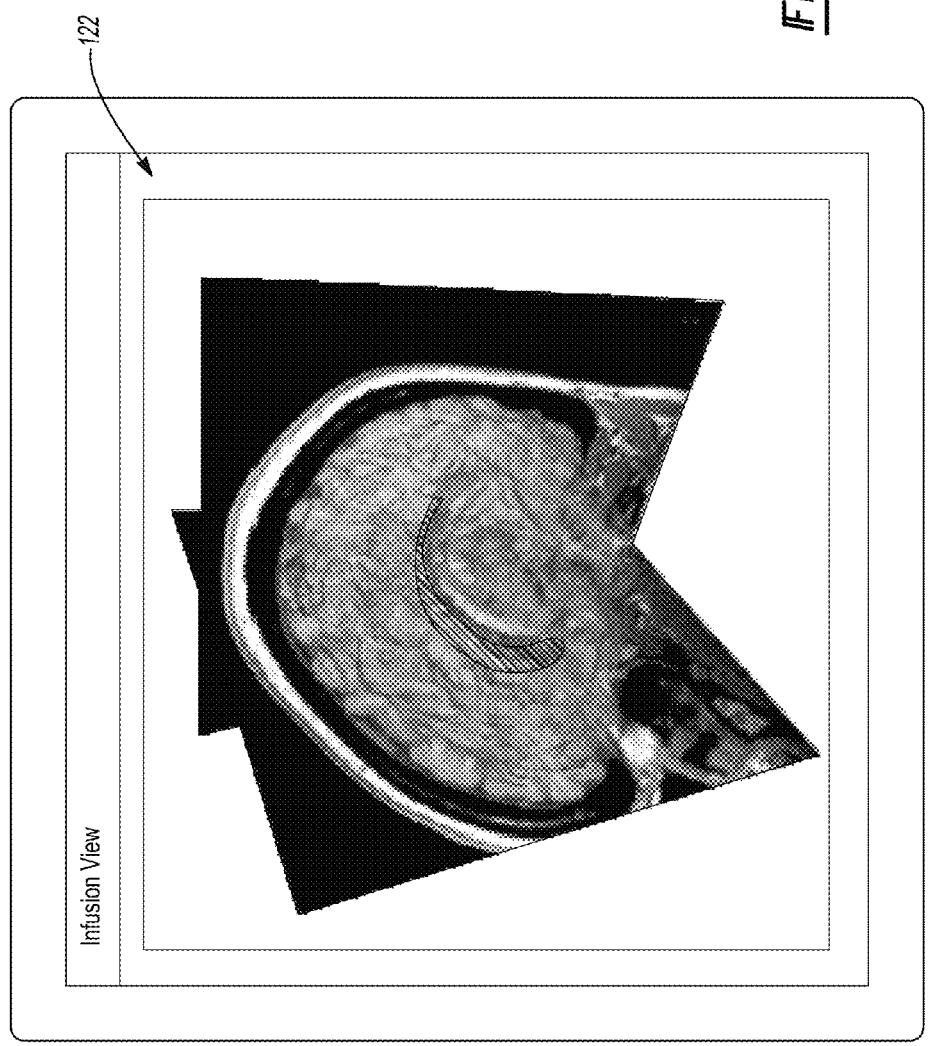
FIG. 6 is a screen shot illustrating a predicted Volume of Efficacy illustrated relative to three-dimensional image data.

The display may only illustrate the predicted VOE or can include or have the VOE super-imposed on image data of the patient or an atlas of a subject. For example, as illustrated in FIG. 6, the predicted VOE can be illustrated relative to three-dimensional image data of a patient, such as superimposed thereon. It is understood, however, that two-dimensional image data can also or alternatively be displayed.

Also, the display 88 and the input 86 can be used to alter or view variations of timing and infusion parameters. As discussed above, the parameters of infusion can be varied. Thus, as illustrated in FIG. 7, a time line 130 can be illustrated. A moveable cursor 132 can be placed on the time line 130. A user can drag the cursor along the time line to view the predicted VOE at different times along the time line, such as viewing the predicted VOE 134 at 11 AM and viewing the predicted VOE 136 at 12:30 PM. Again, the predicted VOE can be illustrated alone on the display or relative to image data.

As discussed above, the PK and PD of a selected material, which will be a treatment substance, can be determined using various techniques. The material can include a molecule of various types that are placed in a carrier substance for direct delivery to a portion of a subject. The subject can include a human patient 440 (illustrated in FIG. 10). The delivery area can be a Region of Interest for Therapy (ROIT) and can include regions in the brain, other neural areas, muscular tissue, or other appropriate tissues. The material can include one or more molecules of a drug, either synthetic or purified from a natural source for delivery to the subject. Molecules can also include genetic or RNA molecules such as synthetic and/or small RNA molecules including inhibitor RNA or small inhibitor RNA (siRNA). The molecules can be delivered to the ROIT to achieve a volume of efficacy (VOE), as discussed above. The VOE can be based upon various parameters and tissue properties or subject properties. The VOE is generally selected to provide for an efficacious volume or concentration of the delivered molecule within a selected volume of the subject. The VOE is generally at least a portion of a Volume of Distribution (VOD). The VOD is the entire volume of tissue that contains any of the material that is delivered to the subject. A Volume of Infusion is the volume or amount of the material that is delivered to the patient over a selected period of time.

The VOE and/or VOD can be modeled in the subject, as discussed further herein, based upon various modeling techniques. The model can predict or determine the VOE of the selected material, including the molecule, within the subject based on various parameters, such as a flow rate and the like for the molecule and/or the carrier substance. Various techniques can be used to identify a best or optimal location of a catheter 400 (Illustrated in FIG. 10) or multiple catheters within a subject to achieve the VOE. It would be understood that the optimal or best parameter or location of a catheter may include a plurality of choices within a range based on cost factor analysis that is presented to a user, such as a surgeon.

In addition to FIG. 7 illustrating a timeline for the VOE over a period of time, FIG. 7 can illustrate the position of the VOE 134 relative to the selected target of the anatomy based upon the complex infusion parameters determined or considered in block 51 of FIG. 1. For example, when the cursor 132 is at 11:00 AM, as illustrated in the top frame of FIG. 7, the VOE 134 relative to the anatomy based upon the complex parameter at time 130*b* is illustrated. The cursor 132 can move to 12:30 AM, as illustrated in the lower frame of FIG. 7, to illustrate the view based upon the complex parameter at time 130*f*. Accordingly, the system can determine the VOE at different periods in time based on time varying infusion parameters. Thus, the VOE can include or be viewed as a time varying VOE. Similarly, the VOD can be determined as varying over time and can be a time-varying VOD.

The VOE can vary over time, as illustrated in FIG. 7, based upon the complex infusion parameters. The complex infusion parameters can include a varying (e.g. time varying) infusion rate, varying (e.g. time varying) concentration of the infused selected material, and other infusion parameters that can vary over time of based on selected criteria. The varying of the infusion parameters, including those discussed above, can achieve a selected VOE that can vary over time based upon the anatomy and the input parameters. The VOE timeline, illustrated in FIG. 7, can therefore be used to illustrate the change of the VOE over time based upon the complex infusion parameters.

In addition to illustrating the complex infusion parameters related to the VOE over time (e.g. varying VOE), the varying VOE can be used to determine the position of a catheter for infusion in the patient to achieve a selected or predetermined VOE relative to the selected anatomical target. For example, the selected anatomical target can be determined to be encompassed by the VOE for a selected period of time, such as a selected number of hours. The timeline in FIG. 7 can be used to illustrate the varying VOE relative to time based upon the complex infusion parameters. Accordingly, the VOE can be modeled over time and illustrated in FIG. 7 to assist in determining the parameters in block 66 for achieving the desired VOE. Accordingly, the varying VOE can vary over time due to the varying infusion parameters, including varying concentration or varying flow rate.

As the infusion parameters can include complex infusion parameters, these complex infusion parameters can be used to model varying VOEs to determine an appropriate location for catheter placement. Also, a varying VOE may be selected for the treatment. Thus, the infusion parameters may not be limited to the infusion parameters based upon a single value for any infusion parameter. The complex infusion parameters can include the varying parameter that can vary over time to allow a VOE that can be based upon a plurality of infusion parameters that can vary over time.

Figure 8:
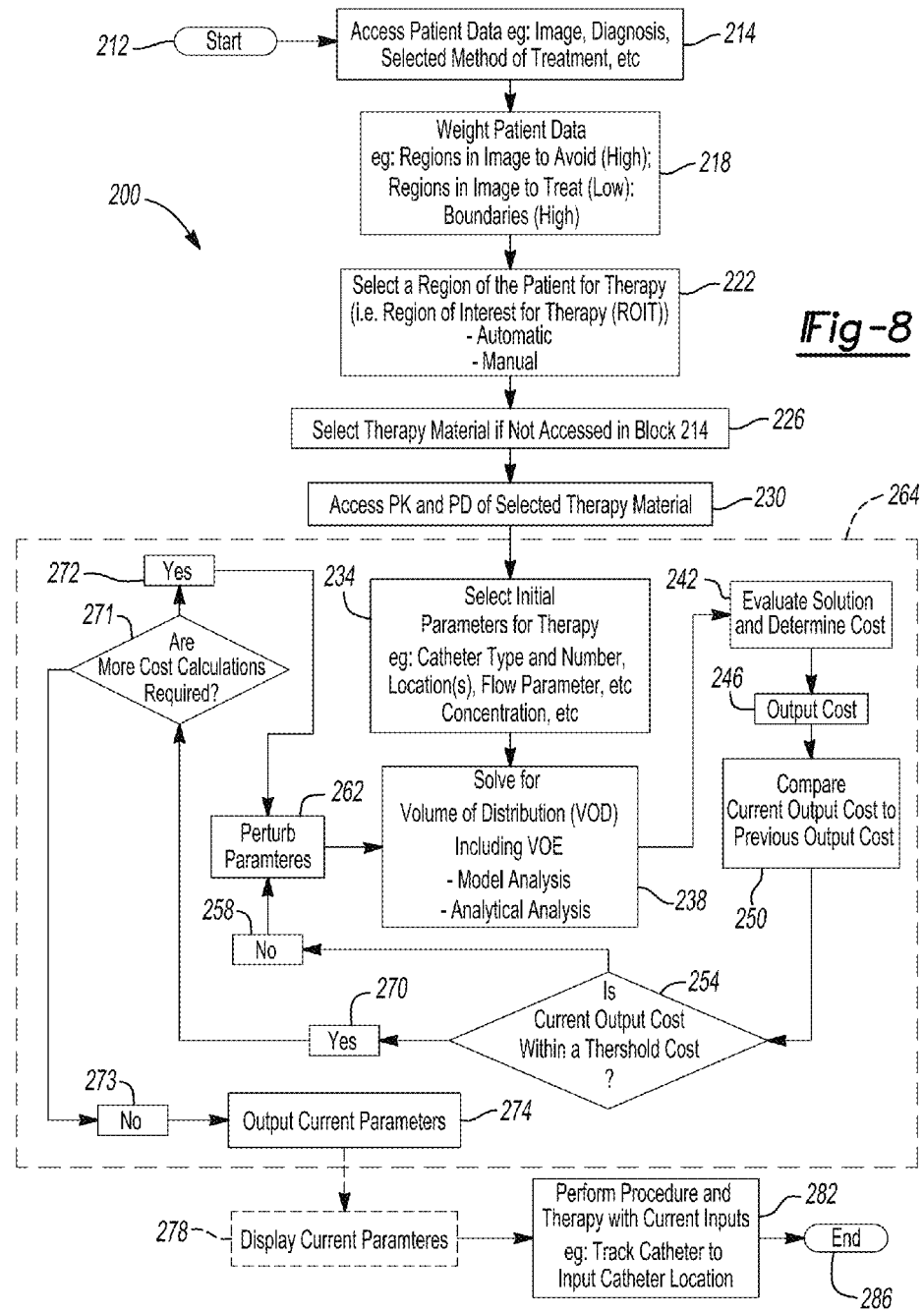
FIG. 8 is a flowchart illustrating a method of determining factors to achieve a selected result.

With reference to FIG. 8, a method to identify an optimal or range of optimal catheter placements to deliver a molecule having a VOE is illustrated in the flowchart 200. The method 200 can also be used to determine various parameters to achieve the VOE at the ROIT, as discussed herein. Generally, however, the optimal location of the catheter can be one of a plurality of possible catheter placements output for selection by a user. In addition, the various cost factor associated with each placement can be output for the user's review.

The method in flowchart 200 can begin in start block 212. The procedure, once started in the flowchart of start block 212, can proceed to accessing a patient's data in block 214. Patient data can include image data of the patient that is acquired at any selected time. For example, prior to beginning a procedure on the patient, image data can be acquired of the patient including three dimensional data created with a computer tomography (CT) scan system, magnetic resonate imaging (MRI), or other appropriate techniques. Additionally, image data can include two dimensional x-ray images, ultrasound images, or other appropriate image data. Patient data can also include identification of a type of tissue or type of region within different regions in the image data. For example, within the brain, identification of grey matter, white matter, blood vessels, and voids (e.g. sulci) can be identified. Additionally, patient data can include a diagnosis of the patient for which treatment is to be made. For example, a diagnosis of Huntington's disease can be made for which a therapy of delivery of siRNA can be made. It is understood that a selected material for treatment can also be selected and input as patient data. For example, a diagnosis may lead to a single treatment material and it may also be input. Other patient data can also include prior treatments, prior injuries, prior treatment location or diseases, or other appropriate patient information.

Once the patient information is accessed and blocked 214, the patient information can be weighted in block 216. In particular, the image data can be weighted based upon identified types of tissue or identification of anatomical features or portions. For example, image data can be weighted based upon a selected cost factor analysis after tissue types and portions of the anatomy have been identified. For example, regions to be avoided can be given a low value, regions to be treated, passed through, or are injured can be given a high value, and boundaries can be given a low-to-medium value, based upon a distance from a region to be avoided. For example, a region to be entered or treated can be given a high value and a boundary between a region to be treated and a region to be avoided can be given the lowest value and for each millimeter away from the boundary into the region to be treated, the cost value can be increased by a selected increment. It will be understood, however, the opposite value may be assigned so that a low value can be given to the region to be treated and a high value given to the region to be avoided, depending upon the selected output for a cost analysis. Accordingly, if a cost analysis is to return a high value for an undesirable treatment and location, then the high cost values can be given to regions to be avoided. If, however, the cost factor analysis is to return a high value for a region to be treated then a high weight value can be given to the image data or patient data that coincides or indicates a region to be treated.

That is, the goal of the cost analysis is to determine a result or selection is a low or a least negative impact on the patient. A negative impact on the patient may have the VOD contact regions that are undesired or contraindicated, a VOE that does not cover the area selected for treatment, a large volume of infusion, a high number of catheters, or other selected negative impacts. For example, therefore, the cost factor analysis can also be used to analyze overflow of the selected material from the ROIT (i.e. the VOD is greater than the ROIT). Also, a region desired to not be within a volume of distribution can be weighted (e.g., to ensure material free volumes within the subject). Regardless of the weighting values, weight values can be assigned to different portions of the data, such as image data of the subject or patient in block 216.

The weighting of the image data can be performed by a surgeon using various known techniques or experience of the surgeon. For example, the surgeon can identify grey and white matter in the brain of the patient. Alternatively, the weighting can be performed substantially automatically by analysis of the image data and other patient data by an appropriate algorithm. The algorithm can identify grey and white matter in the brain image data and other tissue in the patient image data. Alternatively, or in addition thereto, the algorithm can identify or use tractography (e.g. using Diffusion Tensor Image (DTI) data) or other information to identify or weight portions of the imaged data. Alternatively, a combination of automatic and manual techniques can be used to weight the image data. For example, a computer algorithm can segment the image data to identify white matter and grey matter and then a surgeon can apply a weight after viewing and/or verifying the segmented image data. Additionally, the patient data can include tractography and the surgeon can use the tractography image data to further appropriately weight portions of the image data. Accordingly, it is understood that the weighting can be automatic, manual or a combination of automatic and manual weighting.

In the image data, a region can be selected for treatment in block 222. The selection of the region for treatment can be a region of interest (ROI) which can also be referred to as the ROIT. The ROI can be identified in the image data prior to or subsequent to the weighting in block 216. It is understood, however, that the ROI can incorporate the weighting or can be used to assist in weighting. Accordingly, weighting performed in block 216 can be augmented based upon an ROI identified in block 222 or the weighting in block 216 can be based upon at least in part, of the ROI identified in block 222.

The ROI selected in block 222 can be substantially a manual selection, such as identification of a region to be treated by a surgeon. The surgeon can identify a portion of the image data such as the caudate and/or putamen in the brain image data of the patient to which the molecules are to be applied and in or relative to which the VOE is to be achieved. It is also understood, automatic identification of a region for treatment or ROI can be performed substantially automatically with a processor or a computer system executing a selected algorithm (e.g. the processor systems 410 and 420 illustrated in FIG. 10 and discussed below). The algorithm can be used to identify a region to be treated based upon a selected diagnosis. The selected algorithm can include automatic segmentation which can identify anatomical features in image data. Automatic segmentation can include edge detection and/or segmentation routines. The segmented portions can then be identified with atlas data of the selected regions (e.g. identifying regions in the brain with brain atlases). Exemplary algorithms include the SLICER algorithm as disclosed and implemented in the 3D Slicer system at www.slicer.org, incorporated herein by reference. For example, the processor system can identify the caudate in the brain image data of the patient. It is understood the processing system can include the processor 84 or the processor illustrated in FIG. 10. The caudate can be selected for being included, either entirely or partially within the VOE. It is further understood that a combination of automatic and manual ROI selection can be used. Again, a processor system can segment the image data and the surgeon can assist in identifying or determining, based at least in part upon the segmented image, the appropriate ROI for treatment. According to the various embodiments, a region of treatment can be selected in block 222 that can also be referred to as an ROI.

A selection of a material for treatment is made in block 226. The selection of the material can be performed with or at the time of the diagnosis and can be part of the patient information accessed in block 214, as discussed above. Nevertheless the selection of the material for treatment can be selected after or as a part of the planning procedure. In part, the material selected has specific properties, such as pharmacokinetics (PK) and pharmacodynamics (PD), which can be incorporated into the planning process.

Accordingly, once the selection of the material for treatment is made in block 226, the PK and PD of the selected material can be accessed in block 230. Accessing the PK and PD of the selected material can include accessing or retrieving data from a database (e.g. electronically stored and retrieved or a hardcopy) to determine the PK and PD of the selected material. The PK and PD can be determined for a selected material, as discussed above. Briefly, the PK and PD can be based upon experimental processes, including prior infusion into a selected patient, and can be used to assist in planning the location of a catheter placement for a current treatment. Accordingly, accessing the PK and PD in block 230 can include inputting the PK and PD based on information or knowledge of a user, such as a surgeon, or accessing a stored PK and PD for the selected material.

Once the selection of the material is performed in block 226 and the PK and PD of the material is accessed in block 230, an initial set of parameters for the catheter can be selected in block 234. The initial set of parameters can include an initial location, flow rate, flow times and other selected parameters. The parameters selected in block 234 can also be referred to as inputs for the treatment of the patient. For example, flow rate can include high and low flow rates and times at high and low flow rates. Other parameters can also include number of catheters (e.g. one or more catheters), type of catheter (e.g. single outlet, multiple outlet, or porous outlet), and other selected parameters. Moreover, the initial parameters can include complex infusion parameters, as discussed above in block 51 in FIG. 1. Thus, the complex parameters can be considered when solving for the VOE to solve for the varying VOE.

The PK and PD of the selected material and the initial selected parameters can then be used to solve an initial volume of distribution (VOD) in block 238. The volume of distribution can include or encompass the VOE within the ROI. In solving for the VOD and VOE a concentration gradient can be calculated using various mass transit calculations, as discussed herein. The gradient concentrations can also be illustrated, as shown in FIGS. 2 and 5 to illustrate the concentration of the selected material at various locations relative to the selected infusion site.

The solution of the VOD including the VOE can be performed in selected manners with an analysis algorithm. As discussed further herein, at least two examples of the analysis algorithms are disclosed and can include a model analysis, which can include analyzing the flow of the selected material through the region of input from the catheter. As an alternative, or in addition to the modeling analysis, an analytical analysis can also be performed. The analytical analysis can include a less complex analysis of distribution of material substantially in a sphere or forming a sphere from the position of the catheter. Accordingly, solving for the VOE based upon the selected parameters from block 234 can offer a determination of whether the VOE is appropriate for the selected ROIT selected in block 222.

The solution of the VOE (which can also be referred to as a predicted VOE or concentration gradient) in block 238 can be based on an evaluation of the parameters selected in block 234. The solution of the VOE in block 238, therefore, can include an evaluation of the set of treatment parameters (e.g. catheter type and number, catheter position, flow rate and flow duration parameters, etc.) and can be based on comparing the VOE (based on the treatment parameters) to the various regions identified in the patient's anatomy in the image data. This can involve, as briefly discussed above, determining the value of the amount of the VOE overlap with the ROIT of the patient's anatomy to be treated, and also the cost of the amount of VOE and/or VOD overlap with regions of the patient's anatomy to which delivery of the drug substance is to be avoided. The weighting can be according to the relative value of the treatment of the desired region and the relative cost of the undesirable consequences of delivery of the drug substance to regions to be avoided.

The solution determined of the VOE in block 238, based on the treatment parameters of block 234, can then be evaluated in block 242. The evaluation in block 242 of the solution for the VOE can include a determination of a cost value, also referred to as a cost, based upon the solution determined in block 238, which is based on the treatment parameters of block 234. The evaluation of the cost in block 242 can include evaluating the position of the VOE relative to the image data. For example, the total volume of the VOE, the overlap of the VOE with the ROIT, the position of the catheter to achieve the VOE, total mass or volume of the selected material in the anatomy, and other cost factors that can include the weighted input in block 218. For example, the position of the VOE and the position of the boundary of the VOD can be determined relative to the weighted image data weighted in block 218. Once the solution of the VOE, based on the treatment parameters is made in block 238, an evaluation and determination of a cost of the solution is made in block 242. The determined cost can be output of block 246. The weighting of the image data in combination with the solved VOD and/or VOE can be used, based on selected metrics (i.e. cost factors), to determine the cost of the initial parameters from block 234, or perturbed parameters, as discussed herein. The metrics can include overlap of the VOE with the ROIT, distance of the edge of the VOD to tissue selected to not be treated, flow rates and times, loss of drug to outflow paths (such as escape from the brain tissue into the cerebral ventricles, etc. The output of the cost in block 246 can be any appropriate output. Exemplary appropriate outputs include a visual representation of the VOD or VOE, as illustrated in FIG. 2 and at 350 in FIG. 9 and/or a numerical output of the cost. The image output can be analyzed by a user, such as a surgeon, to determine the appropriateness of the position of the VOD and VOE relative to portions of the image data. Alternatively, or in combination therewith, a numerical output can be assigned and provided for a user such as with a display or a hard printout. It will also be understood that the cost for the individual solution from block 238 may not be output, but may be analyzed or saved on an appropriate memory medium for access and/or comparison to other outputs, as discussed further herein.

Figure 9:
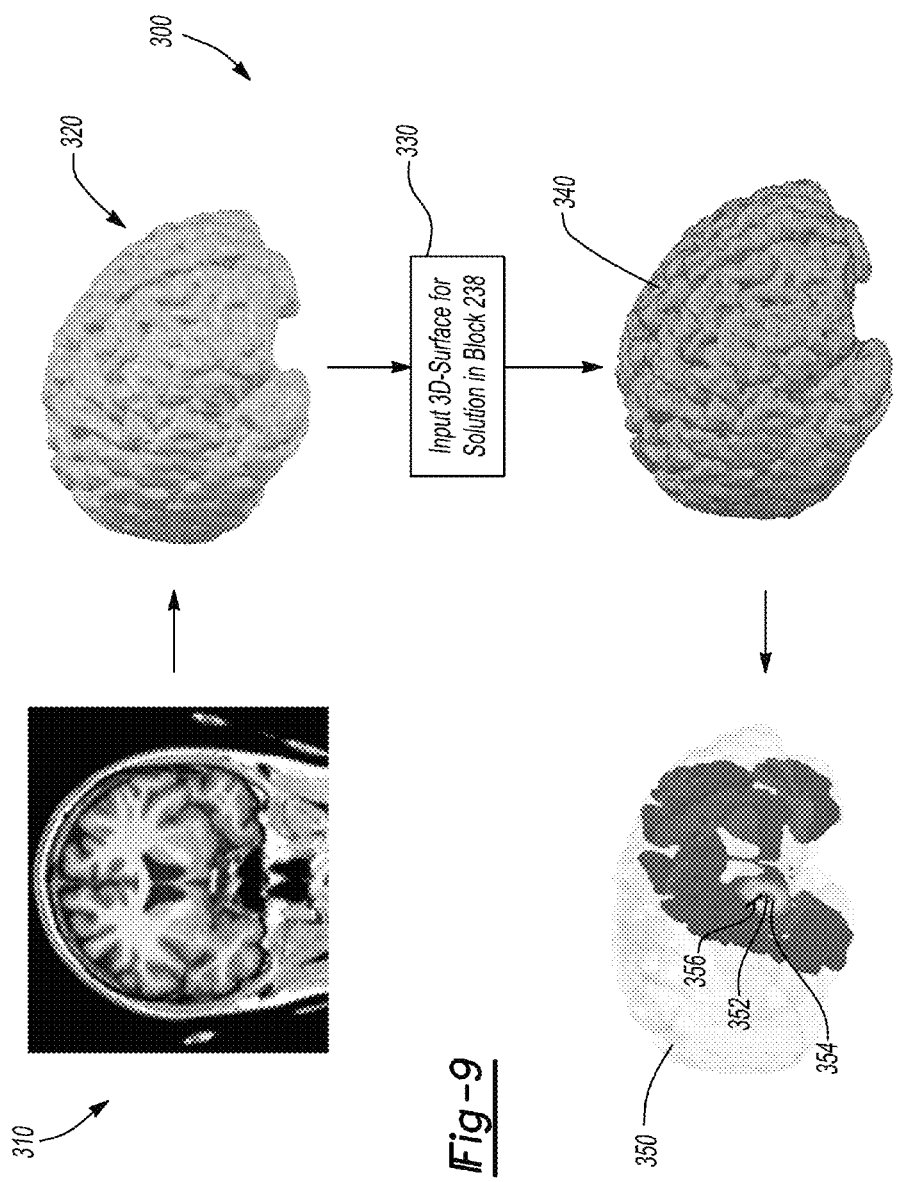
FIG. 9 is a flowchart illustrating an outcome of a selected parameter and a method using image data therefore.

A comparison of a current cost output to a previous cost output can be made in block 250. The comparison can be a comparison of numerical cost values to determine which solution, based on the cost, is more or less negative for a patient outcome. The comparison can also include a visual inspection of a display of an output of the VOD and VOE by the user. The output can include icons that illustrated VOE and VOD, as illustrated in FIG. 9. Alternatively, or in addition thereto, the comparison can include automatically comparing graphical outputs of the VOD and VOE relative to the input image data based upon a comparison of volume and position of boundaries of the VOD and VOE relative to regions of the anatomy and can be automatically analyzed by an algorithm executed by a processor. The inspections by the algorithms can include determining the position of a boundary of the VOD relative to weighted regions of the image data and the comparison can include determining a higher or lower cost of the current cost output and at least one previous cost output.

After comparing the current cost output with the previous cost output in block 250, a decision of whether the current cost is less negative to patient outcome (or a patient outcome cost) than the previous or other determined costs and/or is within a cost threshold can be made in block 254. The cost determination comparison in block 250 can include determining whether one cost is more negative for a patient than another cost based upon the selected parameters. Accordingly, the method 200 can be an iterative sub-process or sub-routine 264 where differing inputs, each of which can result in different costs, can be compared. Accordingly, the decision block 254 can be a determination of whether an optimal and/or selected set of treatment parameters has been found, based on comparison of the cost of the current parameters (e.g. a set of parameters) relative to other parameter sets explored. Negative impact on the patient can include having the VOD encompass unselected areas in the patient, a high number of catheters, etc. As discussed above, a material is to be infused and it may be selected to ensure or attempt to minimize material flow to selected regions of the patient. Thus, a solution of the VOD or VOE that shows flow into unselected areas can include a negative impact for the patient.

The decision block 254 can include generally known minima determination algorithms, such as the Boender-Rinnooy-Stougie-Timmer algorithm (BRST) for finding a global optimum or minima. Generally, as discussed herein, the method 200 can calculate a solution for a range of parameter sets, all possible parameter sets, a volume of infusion locations, etc. Thus, comparing the various possible parameters sets can include determining which one is optimal or minimizes the negative impact on the patient. The decision block 254, therefore, allows for a determination of which parameter set is optimal. Moreover, it is understood, that the sub-routine 264 can generate or output the optimal parameter set and a selected number of sub-optimal, but close to optimal parameter sets.

If the determination in block 254 is that the current cost from the current set of parameters is inappropriate (e.g. not within a threshold, more negative than a previous set, or not enough sets have been evaluated) a NO decision block 258 can be followed to return the parameter set in block 262. Perturbing the parameters can be changing any of the parameters selected in block 234, such as catheter location, flow parameters, and the like, that are different from previously selected parameters in block 234. In perturbing the parameters, the complex infusion parameters can also be perturbed. In this way the complex infusion parameters can be altered, for example, to vary the flowrate and the period over which the varying flowrate is used. Thus, perturbation of the parameters is not limited to only changing a single parameter value or for only one period of time.

Accordingly, after the parameters are perturbed in block 262, a solution for the VOD and/or the VOE can be made in block 238 for the perturbed parameters from block 262. Further, an evaluation of the solution based upon the perturbed parameters can be made in block 242 and an output of costs can be made in block 246. The current cost can then be compared to the previous output cost. The iterative process 264 can be written as a computer algorithm to be executed by the processor system to determine a selected one or plurality of optimal selected parameters (i.e. parameters within a range) to achieve a selected outcome. The selected outcome can be determining the VOE being with the selected ROIT of the patient for treatment selected in block 222.

If the decision block 254 determines that the current cost is within a threshold or includes an improved outcome for the patient over previous costs, then a YES block 270 can be followed to a second decision block of Are more costs required for comparison in block 271. If more costs are required, for example less than a selected number of solutions have been made in block 238, then the YES block 272 can be followed to perturb the parameters further. If no further costs are required for evaluation then a NO block 273 can be followed.

If the NO block 270 is followed then the current set of parameters can be output in block 274. The output of current parameters in block 274 can include parameters such as catheter location, catheter site, flow parameters, and other appropriate parameters for the treatment and can be displayed on a display for a user to assist in selecting and programming a delivery system. For example, a user can select an appropriate catheter, program a pump for infusing the selected material from block 226 through the catheter, and other appropriate parameters.

According to various embodiments, the iterative process described in block 264 can include inputting all possible or a majority of likely parameters for a solution in block 238. For example, only one possible catheter may be used, such as a single outlet catheter or a profusion catheter. Additionally, only a selected number of catheters may be used, such as two or less catheters. Additionally, only the ROIT can be used as the region for possible catheter placements. Also a small or reasonable range of possible flow parameters may be provided, such as a minimum/maximum flow rate and a minimum/maximum time at each of the minimum and maximum flow rates. Accordingly, a set of all possible parameters or inputs can be predefined or defined for solution in block 238. The comparison of outputs in block 250 can then be used to determine or compare all possible outputs based upon the selected parameters. The decision block 254 can then be to identify the best combination of parameters, such as the lowest cost. Also, as discussed above, a cost range can be determined and the combination of parameters within the selected cost range can be output at possible parameters for the procedure. For example, after the output of costs in block 242 the best cost value can be identified in addition to the next five closest cost outputs or ten closest cost outputs to the best cost output as determined by the comparison block 250. The selected range of best cost outputs can then be output in the output of current parameters in block 274. Accordingly, a user can be presented with one or more outputs based upon a selected range or determined appropriate value.

It is further understood, however, that selected algorithms can be used to identify an appropriate iterative procedure at block 264. Accordingly, rather than analyzing all possible or all likely parameters, a selected algorithm can be used to identify the parameters and the best parameters based upon the determination in block 254 can be output in block 274.

Once the output of current parameters is made in block 274 they can be displayed for a user in block 278. It is understood, however, that the parameters may not be displayed in block 278 as they may be simply identified and navigated to, such as with a surgical robotic system. Further, as discussed above, various flow rates and timed flow rates can be part of the parameters. Accordingly, the output of current parameters from block 274, including flow rates, can be directly transferred to the pump system as a program to control the pump to deliver the selected material from block 226 within the selected parameters.

The treatment can then be performed with the current parameters in block 282. The treatment can include navigation of the catheter 400 to the determined and/or selected catheter location. The navigation system 430, illustrated in FIG. 10 and discussed below, can be used to navigate the procedure. The current parameters can be the current parameters from block 274 and can include catheter type, catheter location, high flow rate, timed high flow rate, low flow rate, drug concentration, and timed low flow rate, and other appropriate parameters. The performing of the treatment in block 282 can be an acute or a chronic treatment. For example, a subject can be treated in a single procedure, such as where catheters are positioned within the patient for delivery of the selected material over a relatively short period of time, such as a few hours. Alternatively, a chronic treatment can be provided where a catheter is implanted into a subject and a system is provided, such as an implanted pump, to deliver the selected material over a plurality of days or years. For example, a patient that has been diagnosed with Huntington's Disease can have implanted a catheter at the selected location and a pump can be implanted with the selected material from block 226 where a chronic delivery of the selected materials performed over multiple days and/or years to chronically treat the diagnosed disease. Accordingly, ending the procedure in block 286 can be understood to be completing an acute treatment, such as a single surgical procedure, or completing the implantation and programming of a pump and delivery system for a chronic treatment.

The method described in FIG. 8 can be used according to various solution procedures, as discussed below, and with various iterative selection procedures, also discussed below.

Accordingly, it is understood that method 200 in FIG. 8 can be performed in conjunction with or using selected analysis algorithms (e.g. a model analysis or an analytical analysis) or iterative algorithms as discussed below.

Model Analysis

According to various embodiments, a model analysis, as initially discussed for the solution determination in block 238 and the flowchart 200 can be used as the analysis algorithm to solve the VOD and/or VOE and is generally illustrated in FIG. 9 that illustrates a schematic flowchart 300. In the schematic flowchart 300, image data, such as magnetic resonance image data (MRI) and computed tomography (CT) scan data can be used for the model analysis. The model analysis can use MRI data 310 to generate a 3D surface or three dimensional image model 320 of the image data. As discussed above, the image data can be accessed in block 214 and the image data can be weighted in block 218. Generally, the accessing of patient image data in block 214 can include image data that is either directly from the MRI data in block 310 or the 3D surface data in block 320.

The surface data in block 320 can include identification of not only exterior image model of the brain or other image data, but also substructures within or interior to the exterior surface. For example, if the image data in block 310 is of a brain, substructures can include basal ganglia, including putamen, and caudate substructures. The substructures can be identified in the image data from block 310 using various segmentation techniques. Segmentation techniques can include automatic or algorithm segmentation techniques or manual segmentation techniques, such as segmentation by a user. Automatic segmentation techniques can include matching atlas data to patient image data (e.g. surface matching) to identify structures. Systems to identify structures in image data include label propagation, multi-atlas methods, and probabilistic techniques such as those discussed by Cabezas, M., Oliver, A., Llado, X., Freixenet, J., Caudra, M. B, A review of atlas-based segmentation for magnetic resonance brain images. Computer Methods Programs Biomed. 2011 December; 104(3):e158-77 PMID: 21871688 and/or the SLICER algorithm discussed above, all incorporated herein by reference. Additional data can be provided to assist in segmenting the image data for generating the three-dimensional image surface in block 320. For example, diffusion tensor imaging (DTI) data, atlas models of the brain or other structures can be used to assist in segmenting the image data from block 310 to generate the three dimensional image surface in block 320. For example, the atlas model can be used to identify at least starting regions for segmenting the image data. Segmenting can proceed to an appropriate segmentation algorithm such as those discussed above including the SLICER algorithm. The 3D surface image data from 320 can be parameters for solving the VOD and/or VOE in block 238 as illustrated in block 330 in FIG. 9. The three dimensional surface image data can be the data which is used for the solution in block 238 based on the selected parameters from block 234 or the perturbed parameters from block 262. In the model analysis, the analysis is performed for the specific types of structures that are segmented in the 3D surface data 320 based on the specific equations and analysis discussed below.

According to an example of a model analysis approach, the selected material from block 226 is mass transported into the structure, such as the brain of a patient, through convection and diffusion. The structure of the patient, such as the brain, is a porous media that can be identified or characterized according to various variables that can be determined or selected for the analysis. According to Equation 1 (Eq. 1), as noted above, $$\varphi \frac{\partial c}{\partial t} + \nabla \cdot (vc) = \varphi D \nabla^2 c + S \qquad \text{Eq. 1}$$

a solution for mass transit can be solved. In Equation 1, c is a concentration of the selected material from block 226. Phi (φ) is the porosity of the structure through which the material is being transported and v is the velocity of the selected material from block 226. D is the diffusion coefficient of the selected material from block 226 through the selected materials of the subject identified in the 3D surface image in 320 and S is a sink/source term and t is time. The source/sink term accounts for addition/removal of the selected material from the domain (e.g. within the brain) due to various accounted for causes. For example, accounting for the selected material leaving the brain through arteries might be accounted for in the sink term. If the brain produces its own version of the selected material that is being infused, then this may be accounted for in the source term. Thus, addition and removal of the selected material not related to the effect on the patient or delivery from the infusion source can be accounted for in the model. Various derivations of Eq. 1 include that disclosed in Morrison, et al, High-Flow microinfusion: tissue penetration and pharmacodynamics, AM J Physiol Regulatory Integrative Comp Physiol 266: 292-305, 1994, incorporated herein by reference.

A velocity field v can be solved using Darcy's law, shown in Equation 2 (Eq. 2), $$v = -K \nabla p \qquad \text{Eq. 2}$$

for a porous medium, such as the identified structure in the 3D surface data 320 and substituted into Equation 1. Darcy's law identifies the proportionality of the velocity to the pressure, P, based upon a permeability constant, K. K may, however, be a permeability tensor term (K-bold) as this is the term where incorporation of diffusion tensor from DTI can be made. Herein the same variables are commonly defined and used throughout. Also, in this formulation (e.g. Eq. 1 and Eq. 2), it is assumed that the selected material moves at the same rate as the diluent or carrier material. It may be observed experimentally that the selected material moves more slowly than the diluent. If this is the case, a retardation factor, $f (0 < f < 1)$ can be applied by multiplying the v term to account for the reduced velocity of the selected material with respect to the diluent.

Equations 1 and 2 can be solved with selected numerical techniques for a given domain. The techniques are generally categorized into three categories, including finite-volume, finite-difference, and finite-element methods. According to various embodiments a finite-volume method is used to obtain a solution of Equations 1 and 2 in the 3D surface image 320. For example, a volume of the brain (e.g. the image data of the brain and/or selected voxels, or meshed volumes, as illustrated in FIG. 9) defines the domain upon which a solution is desired. Various examples of algorithms to solve Equations 1 and 2 can include the SIMPLE algorithm which are used in commercial products including FLUENT, sold by ANSYS, Inc. and STAR-CCM+, sold by CD-Adapco, Inc. The SIMPLE algorithm identified or embodied in the noted commercial products identified above can, however, also be used in other codes or software products to solve Equations 1 and 2. The specific software product to solve Equations 1 and 2 is not limited, as long as the 3D surface image 320 can be imported for identification and solution of the Equations 1 and 2.

Once the 3D image data from block 320 is input for solution according to the solution of Equations 1 and 2 discussed above in block 330, the image data can be meshed in block 340. The meshed data in block 340 can identify selected polyhedral shapes within the image to identify the 3D surface and interior structures in the 3D surface image in block 320. Accordingly, all or a portion of the image can be meshed in block 340. The polyhedral shapes can include tetrahedral and hexahedral shapes that generally have contiguous or touching sides with at least one other polygon. The polyhedral shapes that are in the meshed data in block 340 can define the minimum volume location or portion of volume location for specifically positioning the catheter and for solving Equations 1 and 2. Generally, the meshed image data can be used to illustrate and output the solution from block 238 for evaluation in block 242. Generally, therefore, the meshed data in block 340 illustrates the domain in which the Equations 1 and 2 are solved for evaluating the diffusion of the selected material from block 226 according to the input parameters from blocks 234 or 262.

As illustrated in block 350, the data can be used to illustrate an output based upon the evaluation of the solution in block 238. This can also be used to identify a specific location for positioning the one or more catheters or type of catheters to achieve the selected treatment that is performed in block 282. The output can also show a predicted VOE icon 352 that shows the solution of the VOE and/or a predicted VOD icon 354 that shows the solution for the VOD on the display, including super-imposed on the image. Also, an instrument icon 356 can be used to illustrate a location determined for the catheter. According to various embodiments, the model analysis can be used to solve for the flow of the selected material from block 228 into a structure, including the brain of a human patient.

Analytical Analysis

In addition to, or alternative to the model analysis discussed above, the analysis algorithm can include an analytical solution or analysis can be used to determine a distribution of the selected material from block 226 in a subject. As discussed above, the model analysis can include patient-specific information including MRI data and DTI data. The image data, including the DTI data, can be used to segment the image data. After the data is segmented then a model can be constructed and the solution for the mass transit equations can be used to determine the diffusion of the selected material into the various regions of the subject that are imaged and segmented in the image data. However, the computational time and cost using the model analysis can be high, including extensive time to find a solution. Accordingly, an alternative analysis may be desirable depending upon preciseness requirements, user selection, time for solution determination, and other factors. One example is an analytical solution that makes certain assumptions about movement of material into the subject.

Based upon selected factors or information, such as a catheter being placed in a substantially isotropic region including a substantially inclusively grey matter region of a brain, a spherical distribution of the selected material may be assumed. For example, if a catheter is positioned in the head of a putamen, the grey matter thereof is substantially isotropic. Accordingly, the selected material delivered from the catheter can generally be delivered into an essentially or substantially spherical volume within the ROI of the subject. Assuming a substantially spherical distribution of the selected material, spherical coordinates can be used to solve for a distribution of the selected material within the subject.

As discussed above, the selected material is generally infused into a porous medium, such as the brain of a subject. The porous medium, including the tissue of the subject, can have a porosity phi ($\phi$) and a fluid that flows according to Darcy's law, shown in Equation 2 above. In the instance of infusions into a brain and in the example disclosed herein, a steady state case can be solved for to ensure a closed form solution. The steady state is the state where the VOD and VOE in the subject are substantially unchanged over time based upon selected parameters, including flow rates, from the catheter. The VOD and VOE can include both the intracellular space/volume and the extracellular space/volume. The Peclet number shows that convection dominates diffusion for selected flow rates into the subject. Accordingly, the rate of diffusion can be neglected in identifying or determining a solution for the flow into a substantially spherical area. In other words, the rate of the movement of the selected material in the VOE and VOD due to diffusion is negligible compared to the rate due to convection.

In the analytical analysis, the conservation of mass of the selected material is defined by Equation 3

$$\varphi \frac{\partial c}{\partial t} + \nabla \cdot (vc) = \varphi D \nabla^2 c - kc \qquad \text{Eq. 3}$$

Here, the sink term S in Eq. 1 has been replaced with a first-order clearance term ($-kc$). Here k is the determined a kinetic rate constant or clearance rate constant of the selected material from the structure and c is the concentration of the material being provided for treatment (e.g. as a parameter in FIG. 9). Other formulations for the clearance term are possible and follow from an understanding of the biological interactions (including Pk and PD) between the selected material (e.g. a drug) and the brain. Thus, the form of the sink term may be specific to the type of drug being modeled. The first-order sink term shown here is an illustrative example of what would be the simplest case.

Generally, the flux of the infused material through a spherical surface is the same as the infused flow rate through the catheter that is being used to infuse the selected material. Accordingly, the velocity at any radius, r, from the catheter is related to the flow rate via the surface area of the sphere around the catheter according to Equation 4

$$v_r = \frac{Q}{4\pi r^2} \qquad \text{Eq. 4}$$

In Equation 5, Q is the flow rate. At the spherical inlet surface, which has a radius $r_0$, the concentration of the selected material can be specified to be equal to that of the concentration at the catheter, $C_{cath}$. In solving for the concentration of the selected materials in the tissue for the total tissue volume, the boundary condition is the porosity times the concentration of the selected material delivered at the catheter. Accordingly, the extracellular concentration, c, can be defined as a function of the radius as shown by Equation 5.

$$c(r) = \varphi C_{cath} e^{-\frac{4\pi \varphi k}{3Q}(r^3 - r_0^3)} \qquad \text{Eq. 5}$$

In the models for some selected materials, the equation for the mass transport and velocity field may be coupled to a number of differential equations related to the binding of the drug to cell surface receptors, internalization of the selected material into the cell, and interactions inside of the cell with other biologic species (e.g. proteins). For example, a differential equation may be included to include the internalization of the material into the cells in the VOD, allowing for an estimation of both extracellular and intracellular material concentrations. These may be summed to express a total concentration per unit tissue volume.

Equation 6 can then be used to determine the VOE which, as discussed above, is the concentration where a selected material has a concentration at/or above a selected concentration that provides a therapeutic effect. Equation 6 illustrates a derivation and simplification of Eq. 5

$$V_{VOE} = \frac{Q}{\varphi k} \ln\left(\frac{\varphi C_{cath}}{C^*}\right) \qquad \text{Eq. 6}$$

where C* the threshold value of the concentration for the VOE, $C_{cath}$, is the concentration as provided from the catheter (e.g. as one of the parameters from FIG. 9) and allows the VOE to be expressed as the spherical volume in Eq. 6 based on the radius of Eq. 5. Because the concentration of Eq. 5 is a function of a radius, r, due to assuming a substantially spherical distribution, the threshold concentration, C*, is known within the radius, r, for a spherical volume. As shown by Eq. 6 the VOE is linearly proportional to the infusion rate and proportional to the natural log of the infused drug concentration. Accordingly, it is understood that the flow rate can more drastically affect the VOE than the concentration of the selected material.

Sub-Process 264 Analysis

According to various embodiments, the solution for the VOD including the VOE in block 238 can be determined using the model analysis, the analytical analysis, or combinations thereof. The solution can be performed by a computer or processor system executing a set of instructions in an algorithm based upon the analyses disclosed above. The determination of the costs can be made in block 242 based upon the weighting of the data from block 218, including weighting of the image data. The output of the cost and the comparison of the cost in block 246 and block 250 can be used, as discussed below, to determine an optimal or range of optimal locations for the catheter and other appropriate inputs, such as flow rate of the catheter. That is, as discussed above, the sub-process 264 can include a solution algorithm to determine the best cost solution based on any set of inputs. The best cost is generally the cost that includes the least negative impact on the patient. Various solution algorithms can include minima determination algorithm such as gradient decent or searching, particle swarming, or genetic algorithms to determine the best cost. Again the best cost can be a high cost or low cost based upon definition, of weights and parameters as discussed above. The minima algorithms can include methods of searching for, including optimally searching for, optimal input parameters for the perturbation of inputs in block 260.

Performing a Procedure

Figure 10:
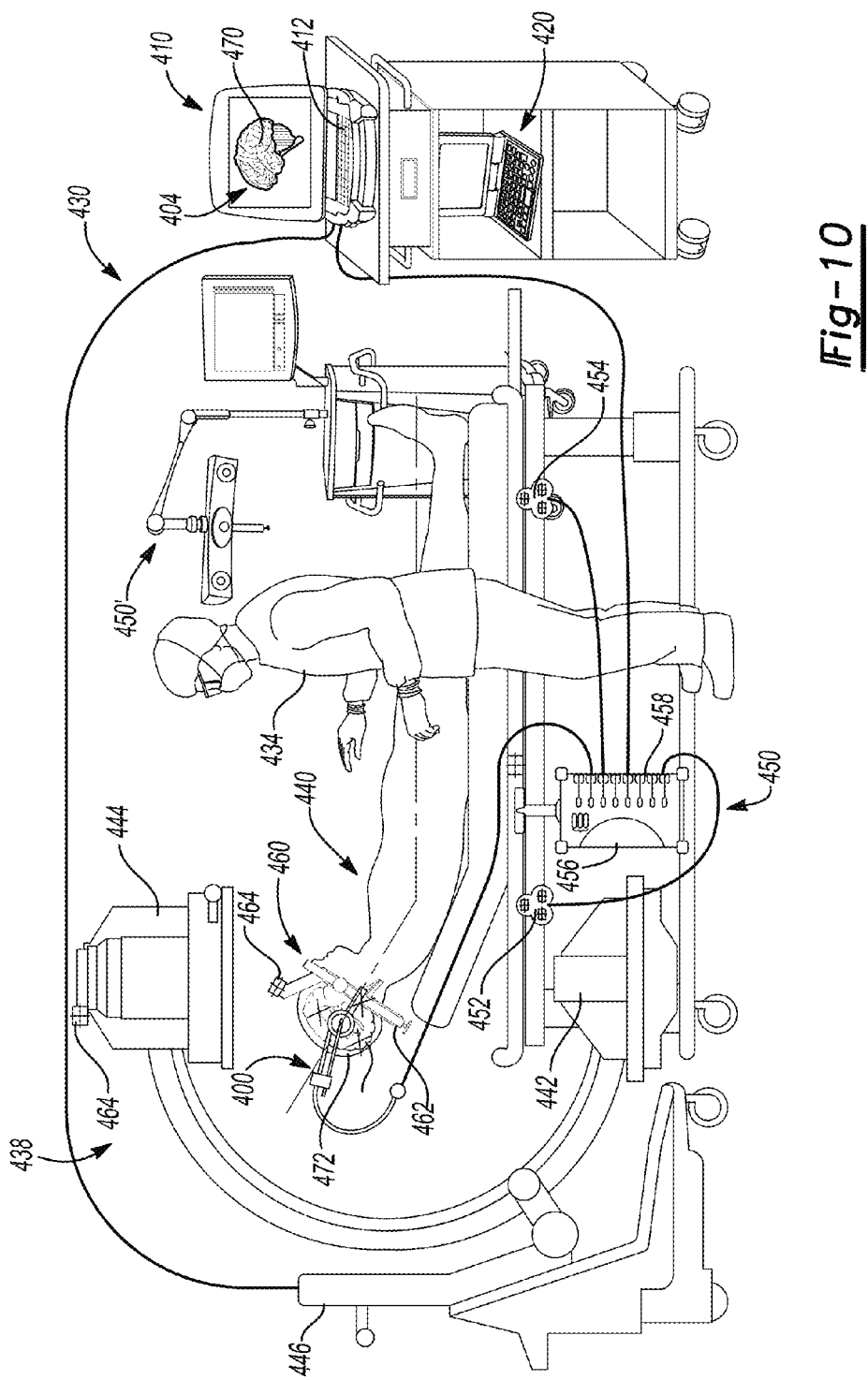
FIG. 10 is a schematic illustration of a procedure navigation system.

The determination of the minima, or other appropriate optimization algorithm, can be determined by portraying the inputs as described above in block 262. The output of current inputs in block 274 can be used for performing the procedure in block 282. As illustrated in FIG. 10, performing a procedure can include tracking an instrument or device, such as a catheter 400, to the catheter location determined in the output of the current input in block 274. It is understood that the output of the current input from block 274 can be displayed on a display screen 404 of a computer or processor system 410. The process system can also be the processor 84 discussed above. The processor system 410 can also include a user input 412 and can display image data 414 on the display 400. The computer system 410 can be a navigational computer alone or a planning system alone, or in combination a navigation processor and a planning processor. Alternatively, it is understood, that a planning processor system 420 can be provided separately that includes user inputs and displays for displaying the selected input from block 274. It is further understood that a navigation system, such as a surgical navigation system 430 can be used to assist in placing the catheter 400. The navigation system 430 can include the navigation system disclosed in U.S. Pat. App. Pub. No. 2010/0240986, incorporated herein by reference.

A user, such as a surgeon 434, can use the algorithm described in flow chart 200 to determine a range of optimal parameters, including a position for the catheter 400 and flow parameters, as described above. The parameters can be based upon the selected material including the predetermined PK and PD to solve for the VOD and VOE. Additionally, the VOD and VOE can be displayed, on the display device 404, for viewing analysis by the user and to assist in determining and/or refining a selected proposed optimal location and the flow parameters of the catheter 400. For example, an optimal location of the catheter 400 determined by the algorithm can be displayed on the display device 404 and the user 434 can alter parameters and the VOD and VOE can be displayed based upon the altered parameters from the user 434 that may not have been within the previously analyzed perturbations in block 262 and/or were not displayed as a part of the optimal or output current inputs from block 274. Also, the user 434 can view the outputs on the display device 404 to determine whether various other metrics are met by the outputs form block 274.

Accordingly, according to various embodiments described above, the user 434 can use the described method and system to determine an optimal or range of optimal locations for the catheter 400 and parameters therefore. The parameters can be used to provide a VOE at a selected location to treat disease. For example, the siRNA can be the selected material and based upon the PK and PD, the method of the flow chart 200, including the subroutine 264, can be used to identify a single or selected range of optimal locations for the catheter along with flow parameters and other selected parameters therefore. Additional parameters can include indicating more than one catheter for infusion of the selected material. The procedure can then occur by either navigating with the navigation system 430 or substantially manually placing the catheter 400. In manual placing, it is understood that the imaging system, such as a C-arm imaging system 438 can be used to position or verify the position of the catheter 400 within the subject, such as a human patient 440. Also, selected stereo-tactic frames and guiding devices can be used in a manual procedure. It is further understood that the procedure can be used for an acute delivery of the selected material (e.g., Less than one day of material flow) or a chronic delivery of the selected material (e.g., greater than 1 day of material flow) and including implantation and programming of reservoir and pump system therefore.

With continuing reference to FIG. 10, the navigation system 430 can be used to track the location of the catheter 400, such as a drug delivery device, relative to the patient 440 to assist in the implementation of the placement of the catheter 400 and implementing the other parameters output in block 274 and/or augmented by the user 434. The navigation system 430 can be used in any appropriate procedure, such as one that is generally minimally invasive, arthroscopic, percutaneous, stereotactic, or an open procedure. Although the navigation system 430 including the optional imaging system 438 are discussed herein, one skilled in the art will understand that the disclosure is merely for clarity of the present discussion and any appropriate imaging system, navigation system, patient specific data, and non-patient specific data can be used.

The navigation system 430 can include the optional imaging device 438 that is used to acquire pre-, intra-, or post-operative or real-time image data of a patient 440. The image data acquired with the imaging device 438 can be used as part of the optimization methods discussed herein. Alternatively various imageless systems can be used or images from atlas models can be used to produce patient images, such as those disclosed in U.S. Pat. No. 7,835,778; issued Nov. 16, 2010, entitled "METHOD AND APPARATUS FOR SURGICAL NAVIGATION OF A MULTIPLE PIECE CONSTRUCT FOR IMPLANTATION", incorporated herein by reference. The optional imaging device 438 is illustrated as a fluoroscopic X-ray imaging device that may be configured as a C-arm having an X-ray source 442, an X-ray receiving section 444, and other parts as generally understood in the art. It is further understood, that other imaging systems can be used to acquire image data pre-, intra-, or post-operative or real-time, such as MRI, CT. An optional imaging device controller 446 may control the imaging device 438. The controller 446 may also be separate from the imaging system 438 and can be part of or incorporated into a processor system 410. The controller 446 can control movement of the imaging system 438 as generally understood in the art. The imaging system 438 can include the fluoroscopic C-arm x-ray device "Series 9600 Mobile Digital Imaging System," from GE Healthcare, (formerly OEC Medical Systems, Inc.) of Salt Lake City, Utah. Other exemplary fluoroscopes include bi-plane fluoroscopic systems, ceiling fluoroscopic systems, cath-lab fluoroscopic systems, fixed C-arm fluoroscopic systems, isocentric C-arm fluoroscopic systems, 3D fluoroscopic systems, an O-arm® Imaging System (sold by Medtronic, Inc.).

While the optional imaging device 438 is shown in FIG. 10, any other alternative 2D, 3D or 4D imaging modality may also be used. For example, any 2D, 3D or 4D imaging device, such as isocentric fluoroscopy, bi-plane fluoroscopy, ultrasound, computed tomography (CT), multi-slice computed tomography (MSCT), magnetic resonance imaging (MRI), high frequency ultrasound (HIFU), positron emission tomography (PET), optical coherence tomography (OCT) (a more detailed discussion on optical coherence tomography (OCT), is set forth in U.S. Pat. No. 5,740,808; issued Apr. 21, 1998, entitled "Systems And Methods For Guiding Diagnostic Or Therapeutic Devices In Interior Tissue Regions" which is hereby incorporated by reference), intra-vascular ultrasound (IVUS), intra-operative CT, single photo emission computed tomography (SPECT), planar gamma scintigraphy (PGS). Addition imaging systems include intraoperative MRI systems, such as the PoleStar® MRI system sold by Medtronic, Inc. Further imaging systems include the O-Arm® imaging system sold by Medtronic, Inc. The images may also be obtained and displayed in two, three, or four dimensions. Four-dimensional surface renderings of regions of the body may also be achieved by incorporating patient data or other data from an atlas or anatomical model map or from pre-operative image data captured by MRI, CT, or echocardiography modalities.

Image datasets from hybrid modalities, such as positron emission tomography (PET) combined with CT, or single photon emission computer tomography (SPECT) combined with CT, could also provide functional image data superimposed onto anatomical data to be used to confidently reach target sights within the patient 440.

Image data, whether acquired with the imaging system 438 or acquired by a different imaging system, can then be accessed by the navigation computer and/or processor system 410 or planning system 420. Moreover, processing for the navigation system and optimization can all be done with a single or multiple processors. In addition, the various processor systems can include or be connected to memory systems to store the image data for analysis and/or store the determined parameters form the flowchart 200.

With continuing reference to FIG. 10, the navigation system 430 can further include an electromagnetic navigation or tracking system 450 that includes a localizer, such as a coil array 452 and/or second coil array 454, a coil array controller 456, a navigated instrument interface 458, the catheter 400, and a dynamic reference frame 460. Exemplary electromagnetic tracking systems can include the StealthStation® AxiEM™ surgical navigation system, sold by Medtronic Navigation, Inc. and those disclosed in U.S. Pat. No. 7,751,865; issued Jul. 6, 2010, and entitled "METHOD AND APPARATUS FOR SURGICAL NAVIGATION", herein incorporated by reference. Other tracking systems can include optical tracking systems 450', exemplary optical tracking systems include the StealthStation® Treon® and the StealthStation® Tria® both sold by Medtronic Navigation, Inc. The dynamic reference frame 460 can include a dynamic reference frame holder 462 and a removable tracking device 464. Alternatively, the dynamic reference frame 460 can include a tracking device 464 that is formed integrally with the dynamic reference frame holder 462.

The tracking device 464 or any appropriate tracking device as discussed herein, can include both a sensor, a transmitter, or combinations thereof. Further, the tracking devices can be wired or wireless to provide a signal or emitter or receive a signal from a system. Nevertheless, the tracking device can include an electromagnetic coil to sense a field produced by the localizing arrays 452, 454 or reflectors that can reflect a signal to be received by the optical localizer 450'. Nevertheless, one will understand that the tracking device can receive a signal, transmit a signal, or combinations thereof to provide information to the navigation system 430 to determine a location of the tracking device 464. An imaging system tracking device 466 can also be used to tracking the imaging system 438. The navigation system can then determine a position of the instrument or tracking device to allow for navigation relative to the patient and patient space. Other tracking systems include acoustic, radiation, radar, infrared, etc. The optical localizer can transmit and receive, or combinations thereof.

The coil array 452, 454 is controlled or driven by the coil array controller 456. The coil array controller 456 can drive each coil in the coil array 452, 454 in a time division multiplex or a frequency division multiplex manner. In this regard, each coil may be driven separately at a distinct time or all of the coils may be driven simultaneously with each being driven by a different frequency. Upon driving the coils in the coil array 452, 454 electromagnetic fields are generated within the patient 440 in the area where the medical procedure is being performed, which is again sometimes referred to as patient space. The electromagnetic fields generated in the patient space induce currents in the tracking device positioned on or in the catheter 400. These induced signals from the tracking device are delivered to the navigation probe interface 458 and subsequently forwarded to the coil array controller 456. An additional representative alternative localization and tracking system is set forth in U.S. Pat. No. 5,983,126, entitled "Catheter Location System and Method," issued Nov. 9, 1999, which is hereby incorporated by reference. Alternatively, the localization system may be a hybrid system that includes components from various systems.

Briefly, the navigation system 430 operates as follows. The navigation system 430 creates a translation map between all points in the image data, such as the image data generated from the imaging device 438 which can include external and internal portions, and the corresponding points in the patient's anatomy in patient space. The image data can include image data 470 illustrated on the display device 404. After this map is established, whenever the tracked catheter 400 is used, the processor system 410 uses the translation map to identify the corresponding point on the acquired image or atlas model, which is displayed on display device 404. This identification is known as navigation or localization. An icon representing the localized point or instruments can be shown on the display device 404 within several two-dimensional image planes, as well as on three and four dimensional images and models. In addition, the VOD and/or VOE can be displayed on the display device 404, such as the view 350.

To enable navigation, the navigation system 430 must be able to detect both the position of the patient's anatomy and the position of the catheter 400 (e.g. the tracking device attached to the catheter 400). This is generally done by patient space to image space registration, as is generally understood in the art and as exemplarily disclosed in U.S. Pat. No. 6,381,485, entitled "Registration of Human Anatomy Integrated for Electromagnetic Localization," issued Apr. 30, 2002 and/or U.S. Pat. No. 7,570,791, entitled "Method and Apparatus for Performing 2D to 3D Registration" issued on Aug. 4, 2009, both hereby incorporated by reference. The system 10 may also perform registration using anatomic surface information or path information as is known in the art (and may be referred to as auto-registration). Knowing the location of these two items allows the navigation system 430 to compute and display the position of the catheter 400 or any portion thereof in relation to the patient 440. The tracking system 450 is employed to track the catheter 400 and the anatomy simultaneously.

According to various embodiments, the DRF 460 can be fixed to a cranium 472 of the patient 440. To obtain a maximum reference it can be selected to fix the dynamic reference frame 460 in each of at least 6 degrees of freedom. Thus, the dynamic reference frame 460 can be fixed relative to axial motion X, translational motion Y, rotational motion Z, yaw, pitch, and roll relative to the portion of the patient 440 to which it is attached. Any appropriate coordinate system can be used to describe the various degrees of freedom. Fixing the dynamic reference frame relative to the patient 440 in this manner can assist in maintaining maximum accuracy of the navigation system 430.

The catheter 400 can include the tracking device at any appropriate position, such as near a distal end of the instrument 400. By positioning the tracking device near the distal end of the instrument 400 knowing or determining a precise location of the distal end can be efficient. Determining a position of the distal end of the instrument 400 can be used to achieve various results, such as determining a precise position of the distal end of the instrument 400, a precise movement of the distal end of the instrument 400. For example, the output from block 274 can include a substantially precise location within the patient 440 for the infusion portion of the catheter

400. Thus, navigating and tracking the infusion tip of the catheter 400 within the patient 440 can be performed by tracking the distal tip.

The catheter 400 can be navigated, as discussed above, to an optimized delivery point as output in block 274 in FIG. 8, within the patient 440. The optimized delivery point and other parameters can be determined according to various methods, discussed herein, substantially automatically, as with the optimization processor 420, or with user input. The optimized delivery parameters can be within a region of interest for therapy (ROIT) as identified in block 222. From the optimized delivery point, a therapy can be delivered, such as delivering a material, including a pharmaceutical, delivery of stem cells or other tissue, or other appropriate therapies. The ROIT can be a physical location within the patient 440 and can be identified in image data of the patient 440. The catheter 400 can then be navigated to the optimized delivery point in the patient 440.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of determining one or more parameters for a treatment within a specific patient, comprising:
   accessing patient specific information including image data having an identified region of interest for therapy in the image data;
   accessing material specific information of a selected material;
   accessing a first flow parameter;
   accessing a first catheter location;
   determining at least one of a first volume of distribution or a first volume of efficacy of the selected material based at least on one of the accessed patient specific information, accessed material specific information, accessed first flow parameter, or accessed first catheter location;
   determining a first cost of the determined at least one of the first volume of distribution or the first volume of efficacy of the selected material;
   determining a second cost of a determined at least one of a second volume of distribution or a second volume of efficacy of the selected material; and
   comparing the determined first cost and the determined second cost.

2. The method of claim 1, wherein the first flow parameter includes a non-time varying value as the first flow parameter.

3. The method of claim 2, further comprising:
   weighting the accessed image data;
   wherein the first cost is based at least in part on the weighted image data.

4. The method of claim 3, wherein weighting the accessed image data is based on a segmentation of the accessed image data.

5. The method of claim 3, further comprising:
   outputting a plurality of possible catheter locations within the specific patient based on a threshold amount from an optimal cost;
   wherein at least determining at least one of the first volume of distribution or the first volume of efficacy of the selected and determining the first cost is determined by executing an algorithm with a processor;
   wherein outputting the plurality of possible catheter locations is also determined based on executing an algorithm with the processor.

6. The method of claim 2, wherein accessing material specific information includes accessing pharmacodynamics and pharmacokinetics of the selected material.

7. The method of claim 2, further comprising:
   outputting the cost.

8. The method of claim 7, wherein outputting the cost includes displaying on a display device an icon representing a volume of the determined at least one of the volume of distribution or the volume of efficacy of the selected material within the specific patient.

9. The method of claim 2, further comprising:
   wherein determining the second cost, includes:
   accessing a second flow parameter;
   accessing a second catheter location;
   determining at least one of a second volume of distribution or a second volume of efficacy of the selected material based at least on one of the accessed patient specific information, accessed material specific information of the selected material, accessed second flow parameter, or accessed second catheter location.

10. The method of claim 9, wherein the second flow parameter includes a non-time varying value as the second flow parameter.

11. The method of claim 10, further comprising:
    automatically determining the first flow parameter, the second flow parameter, the first catheter location, and the second catheter location.

12. The method of claim 10, further comprising:
    outputting the determined first cost or the determined second cost that has a lower negative impact on the specific patient.

13. A method of determining one or more parameters for a treatment within a specific patient, comprising:
    accessing patient specific information including image data having an identified region of interest for therapy in the image data;
    accessing material specific information of a selected material;
    accessing a first flow parameter;
    accessing a first catheter location;
    determining at least one of a first volume of distribution or a first volume of efficacy of the selected material based at least on one of the accessed patient specific information, accessed material specific information, accessed first flow parameter, or accessed first catheter location; and
    determining a first cost of the determined at least one of the first volume of distribution or the first volume of efficacy of the selected material;
    wherein determining at least one of the first volume of distribution or the first volume of efficacy of the selected material includes performing an analytical analysis of a mass transit of the selected material into the specific patient based on a substantially spherical distribution of the first volume of distribution or the first volume of efficacy of the selected material.

14. The method of claim 2, further comprising:
    segmenting the image data of the specific patient;
    identifying a specific type of tissue in the segmented image data of the specific patient; and
    wherein determining at least one of the first volume of distribution or the first volume of efficacy of the selected material includes performing a model analysis of a mass transit of the selected material into the specific patient based at least on the identified specific type of tissue.

15. A method of determining one or more parameters for a treatment within a specific patient, comprising:
accessing patient specific information including image data having an identified region of interest for therapy in the image data;
accessing, for a selected material, at least a pharmacodynamic property and a pharmacokinetic property within a tissue of the patient within the identified region of interest for therapy in the image data;
executing instructions with a processor to:
determine a first volume of efficacy of the selected material based at least in part on the accessed patient specific information, accessed pharmacodynamic property and pharmacokinetic property, a first flow parameter, and a first catheter location,
determine a first cost of the determined first volume of efficacy of the selected material,
determine a second volume of efficacy of the selected material based at least in part on the accessed patient specific information, accessed pharmacodynamic property and pharmacokinetic property, a second flow parameter, and a second catheter location,
determine a second cost of the determined second volume of efficacy of the selected material, and
output at least one of the first catheter location or the second catheter location.

16. The method of claim 15, further comprising:
accessing the first flow parameter; and
accessing the first catheter location.

17. The method of claim 16, further comprising:
executing further instructions with the processor system to automatically determine the second flow parameter and the second catheter location.

18. The method of claim 17, wherein executing instructions with the processor system to output at least one of the first catheter location or the second catheter location includes comparing the first cost and the second cost to determine a less negative impact cost of the first cost or the second cost and outputting the first catheter location or the second catheter location related to the less negative impact cost.

19. The method of claim 18, wherein executing instructions with the processor to determine the first volume of efficacy of the selected material and determine the second volume of efficacy of the selected material includes performing a model analysis of a mass transit of the selected material into the tissue of the specific patient from the respective first catheter location and the second catheter location.

20. The method of claim 18, wherein executing instructions with the processor to determine the first volume of efficacy of the selected material and determine the second volume of efficacy of the selected material includes performing an analytical analysis of a mass transit of the selected material into the tissue of the specific patient from the respective first catheter location and the second catheter location.

21. A system to determine one or more parameters for a treatment within a specific patient, comprising:
a memory system having stored therein an analysis algorithm to analyze pharmacodynamics and pharmacokinetics of a selected material in a selected anatomical tissue to determine a predicted Volume Of Efficacy (VOE) of the selected material within the specific patient;
an input system to input a patient specific information including a patient specific image data;
a processor to access the memory system and execute instructions of the analysis algorithm to determine a patient specific predicted VOE;
a display to display an icon representing the patient specific predicted VOE; and
a user input to input a patient specific target defined in the patient specific image data;
wherein the processor is configured to determine the patient specific predicted VOE that substantially encompasses the input patient specific target in the predicted patient specific VOE when executing the instructions of the analysis algorithm.

22. The system of claim 21, wherein the processor is further operable to execute instructions to determine a cost of a location of a catheter, where the catheter is configured to deliver the selected material to a specific initial location and the selected material is able to diffuse into the specific patient from the specific initial location.

23. The system of claim 21, wherein the processor is further configured to execute instructions to compare a plurality of cost, wherein each cost of the plurality of cost is related to a distinct location of the catheter in the specific patient.

24. The system of claim 23, wherein the cost is based at least in part on a weighting of an image data stored in the memory system, wherein the image data is of the specific patient.

25. The system of claim 21, further comprising:
a catheter configured to be paced at a specific location within the patient to achieve a patient VOE;
wherein the specific location is based on the determined predicted VOE of the selected material within the specific patient.

26. A method of determining a cost of a set of parameters for a treatment within a specific patient, comprising:
accessing patient specific information including image data having an identified region of interest for therapy in the image data;
accessing material specific information of a selected material;
accessing a first set of parameters;
determining a first cost of the accessed first set of parameters for the selected material based at least on a determined at least one of a first volume of distribution or a first volume of efficacy of the selected material;
determining a second cost;
comparing the determined first cost and the determined second cost; and
determining the optimal cost of the first cost and the second cost.

27. The method of claim 26, wherein the first set of parameters includes a flow parameter through a catheter into the patent and a catheter location of the catheter within the patient.

28. The method of claim 27, further comprising:
determining at least one of the first volume of distribution or the first volume of efficacy of the selected material based at least on one of the accessed patient specific information, accessed material specific information, and accessed first set of parameters.

29. The method of claim 28, further comprising:
accessing a second set of parameters; and
wherein determining the second cost of the accessed second set of parameters for the selected material based at least on a determined at least one of a second volume of distribution or a second volume of efficacy of the selected material.

30. A method of determining one or more parameters for a treatment within a specific patient, comprising:
- accessing patient specific information including image data having an identified region of interest for therapy in the image data;
- accessing material specific information of a selected material;
- accessing a first time-varying flow parameter that includes a set of flow parameter values that differ over time;
- accessing a first catheter location;
- determining at least one of a first time-varying volume of distribution or a first time-varying volume of efficacy of the selected material based at least on the accessed patient specific information, accessed material specific information, accessed first time-varying flow parameter, and accessed first catheter location; and
- determining a first cost of the determined at least one of the first time-varying volume of distribution or the first time-varying volume of efficacy of the selected material;
- wherein the first time-varying flow parameter that includes a set of flow parameter values that differ over time includes at least a one of a first flow rate that includes a first initial flow rate at a first time and a first subsequent flow rate at a second time later than the first time or a first concentration that includes at least a first initial concentration at a first time and a first subsequent concentration at a second time later than the first time.

31. The method of claim 30, further comprising:
- outputting a plurality of possible catheter locations within the specific patient based on a threshold amount from an optimal cost;
- wherein at least determining at least one of the first time-varying volume of distribution or the first time-varying volume of efficacy of the selected material and determining the first cost is determined by executing an algorithm with a processor;
- wherein outputting the plurality of possible catheter locations is also determined based on executing an algorithm with the processor.

32. The method of claim 30, outputting the first cost at least by displaying on a display device a variable icon representing a time-varying volume of the determined at least one of the first time-varying volume of distribution or the first time-varying volume of efficacy of the selected material within the specific patient.

33. The method of claim 32, further comprising:
- accessing a second time-varying flow parameter that includes a set of flow parameter values that differ over time;
- accessing a second catheter location;
- determining at least one of a second time-varying volume of distribution or a second time-varying volume of efficacy of the selected material based at least on one of the accessed patient specific information, accessed material specific information of the selected material, accessed second flow parameter, or accessed second catheter location;
- determining a second cost of the determined at least one of the second time-varying volume of distribution or the second time-varying volume of efficacy of the selected material; and
- comparing the determined first cost and the determined second cost.

34. The method of claim 33, wherein the second time-varying flow parameter that includes a set of flow parameter values that differ over time includes at least a one of a second flow rate that includes a second initial flow rate at a first time and a second subsequent flow rate at a second time later than the first time or a second concentration that includes at least a second initial concentration at a first time and a second subsequent concentration at a second time later than the first time.

35. The method of claim 34, further comprising:
- automatically determining the first time-varying flow parameter, the second time-varying flow parameter, the first catheter location, and the second catheter location.

36. The method of claim 33, wherein determining at least one of the first time-varying volume of distribution or the first time-varying volume of efficacy of the selected material includes performing an analytical analysis of a mass transit of the selected material into the specific patient based on a substantially spherical distribution of the first time-varying volume of distribution or the first time-varying volume of efficacy of the selected material.

37. The method of claim 33, further comprising:
- segmenting the image data of the specific patient;
- identifying a specific type of tissue in the segmented image data of the specific patient; and
- wherein determining at least one of the first time-varying volume of distribution or the first time-varying volume of efficacy of the selected material includes performing a model analysis of a mass transit of the selected material into the specific patient based at least on the identified specific type of tissue.

* * * * *